(12) United States Patent
Palmer

(10) Patent No.: US 12,076,506 B2
(45) Date of Patent: Sep. 3, 2024

(54) STERILE URINARY CATHETER PACKAGE WITH DISPENSING SYSTEM

(71) Applicant: Cure Medical LLC, Newport Beach, CA (US)

(72) Inventor: Timothy A. Palmer, Stillwater, MN (US)

(73) Assignee: ConvaTec Inc, Bridgewater, NJ (US)

( * ) Notice: Subject to any disclaimer, the term of this patent is extended or adjusted under 35 U.S.C. 154(b) by 813 days.

(21) Appl. No.: 17/230,547

(22) Filed: Apr. 14, 2021

(65) Prior Publication Data

US 2021/0228837 A1 Jul. 29, 2021

Related U.S. Application Data

(63) Continuation-in-part of application No. 16/428,573, filed on May 31, 2019, now Pat. No. 10,980,974, which is a continuation-in-part of application No. 16/111,779, filed on Aug. 24, 2018, now Pat. No. 10,315,008, which is a continuation-in-part of application No. 15/671,341, filed on Aug. 8, 2017, now Pat. No. 10,814,097.

(51) Int. Cl.
*A61M 25/00* (2006.01)
*A61M 1/00* (2006.01)
*A61M 25/01* (2006.01)

(52) U.S. Cl.
CPC .......... *A61M 25/0147* (2013.01); *A61M 1/69* (2021.05); *A61M 1/84* (2021.05); *A61M 25/0017* (2013.01); *A61M 25/002* (2013.01)

(58) Field of Classification Search
CPC .......... A61M 25/0147; A61M 25/0017; A61M 15/002; A61M 25/0111; A61M 25/0113
See application file for complete search history.

(56) References Cited

U.S. PATENT DOCUMENTS

| 1,206,655 A | 11/1916 | Belcher |
| 2,131,956 A | 10/1938 | Jones |

(Continued)

FOREIGN PATENT DOCUMENTS

| EP | 2703036 A2 | 3/2014 |
| FR | 2085115 A5 | 12/1971 |
| FR | 2794638 | 12/2000 |

OTHER PUBLICATIONS

European Union Intellectual Property Office, Search Report for European Application No. 19191071.0-1132, mail date Jan. 22, 2020, 8 total pages.

*Primary Examiner* — Jessica Arble
(74) *Attorney, Agent, or Firm* — TAFT STETTINIUS & HOLLISTER LLP; Ryan O. White; Derek B. Lavender

(57) ABSTRACT

A packaged closed intermittent urinary catheter system equipped with a dispensing system and method of dispensing a packaged catheter using the dispensing system. The dispensing system is a pair of separately translatable movement control devices, each operably engaging the catheter for permitting unidirectional movement of the catheter in a first axial direction relative to the movement control devices. The movement control devices may be mounted to a hand-grippable assembly with a sliding or pivoting movable member reciprocal to a base member. Alternatively, the movement control devices are mounted to a coupling member and a spring member biases them apart.

20 Claims, 32 Drawing Sheets

(56) References Cited

U.S. PATENT DOCUMENTS

| | | |
|---|---|---|
| 2,221,801 A | 11/1940 | Keppinger |
| 2,422,891 A | 6/1947 | Dickson |
| 2,584,644 A | 2/1952 | Verdi |
| 1,894,119 A | 7/1959 | Stenger |
| 3,365,761 A | 1/1968 | Kalvig |
| 4,140,127 A | 2/1979 | Cianci et al. |
| 4,141,452 A | 2/1979 | Martin et al. |
| 4,230,115 A | 10/1980 | Walz, Jr. et al. |
| 4,451,256 A | 5/1984 | Weikl et al. |
| 4,811,847 A | 3/1989 | Reif et al. |
| 5,108,066 A | 4/1992 | Lundstrom |
| 5,224,681 A | 7/1993 | Lundstrom |
| D358,679 S | 5/1995 | Garrity |
| 5,454,798 A | 10/1995 | Kubalak et al. |
| 5,529,148 A | 6/1996 | O'Laery |
| 5,603,702 A | 2/1997 | Smith et al. |
| 5,690,645 A | 11/1997 | Van Erp |
| 5,993,437 A | 11/1999 | Raoz |
| 6,004,305 A | 12/1999 | Hursman et al. |
| 6,010,105 A | 1/2000 | Davis |
| 6,053,905 A | 4/2000 | Daignault, Jr. et al. |
| 6,179,514 B1 | 1/2001 | Cheng |
| 6,402,726 B1 | 6/2002 | Genese |
| 6,427,964 B1 | 8/2002 | Hillstrom et al. |
| 6,578,709 B1 | 6/2003 | Kavanagh et al. |
| 7,094,220 B2 | 8/2006 | Tanghoj et al. |
| 7,458,964 B2 | 12/2008 | Mosler et al. |
| 7,476,223 B2 | 1/2009 | McBride |
| 7,985,217 B2 | 7/2011 | Mosler et al. |
| 8,734,426 B2 | 5/2014 | Ahmed et al. |
| 9,707,375 B2 | 7/2017 | Conway et al. |
| 9,782,563 B2 | 10/2017 | Palmer |
| 9,884,167 B2 | 2/2018 | Gustavsson |
| 9,987,464 B1 * | 6/2018 | Donald ............... A61M 27/00 |
| 10,099,032 B2 | 10/2018 | Gustavsson et al. |
| 10,226,596 B1 | 3/2019 | Dyall |
| 10,315,008 B2 | 6/2019 | Palmer |
| 2003/0050653 A1 | 3/2003 | Berger |
| 2007/0073222 A1 | 3/2007 | Lilley et al. |
| 2007/0088330 A1 | 4/2007 | House |
| 2007/0225649 A1 | 9/2007 | House |
| 2008/0103464 A1 | 5/2008 | Mosler et al. |
| 2012/0168324 A1 | 7/2012 | Carleo |
| 2012/0239005 A1 | 9/2012 | Conway et al. |
| 2013/0144271 A1 | 6/2013 | Passadore et al. |
| 2014/0257250 A1 | 9/2014 | Palmer |
| 2015/0352324 A1 | 12/2015 | Palmer |
| 2016/0193443 A1 * | 7/2016 | Palmer ............ A61M 25/0017 206/210 |

* cited by examiner

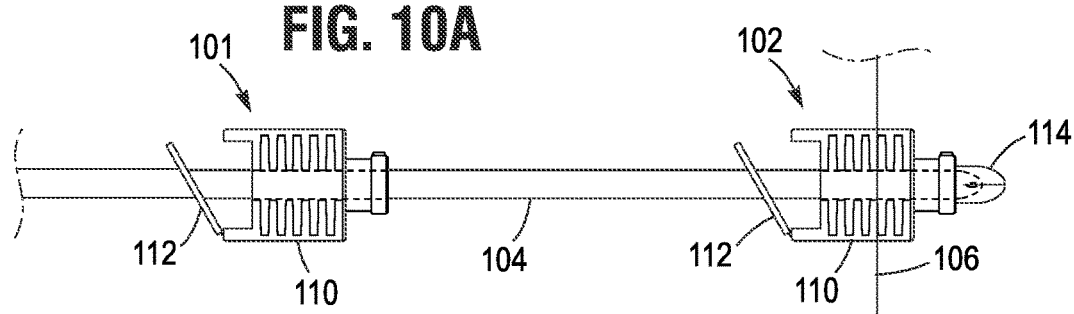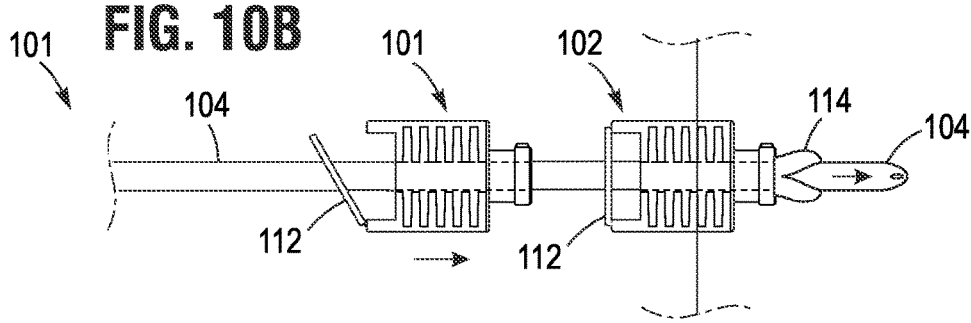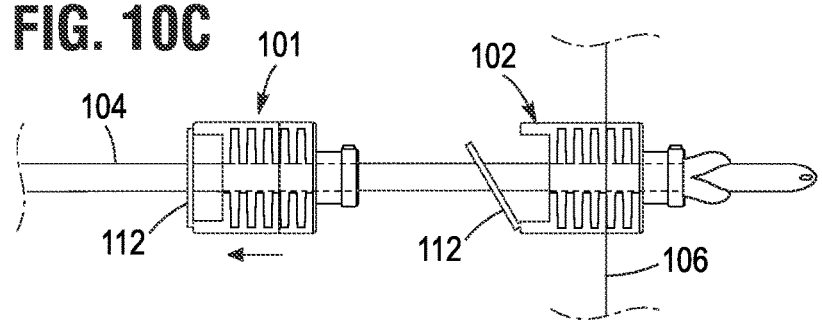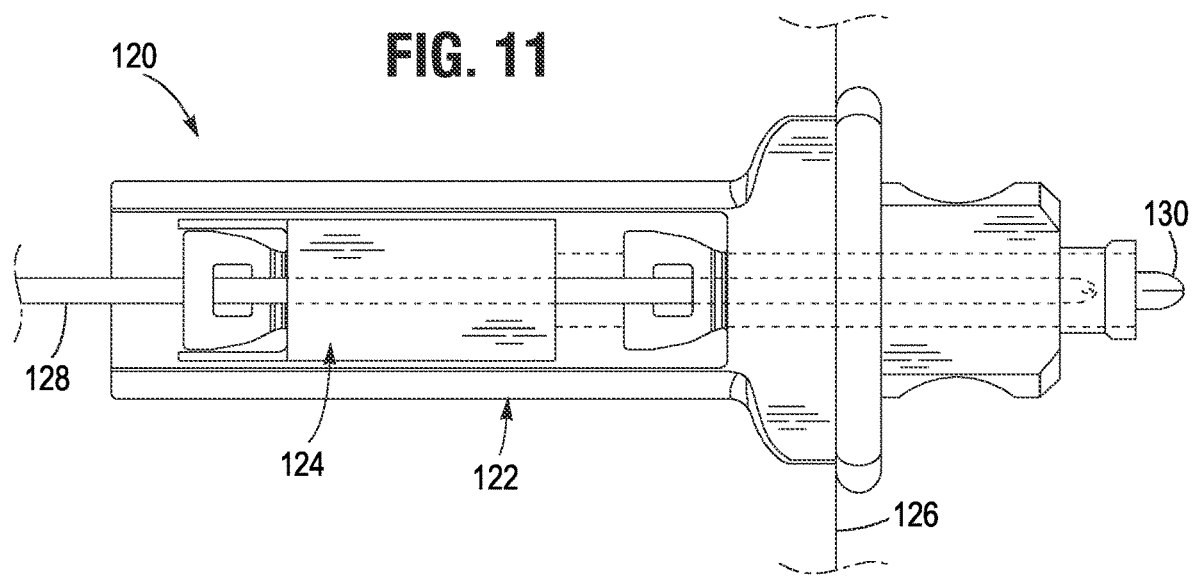

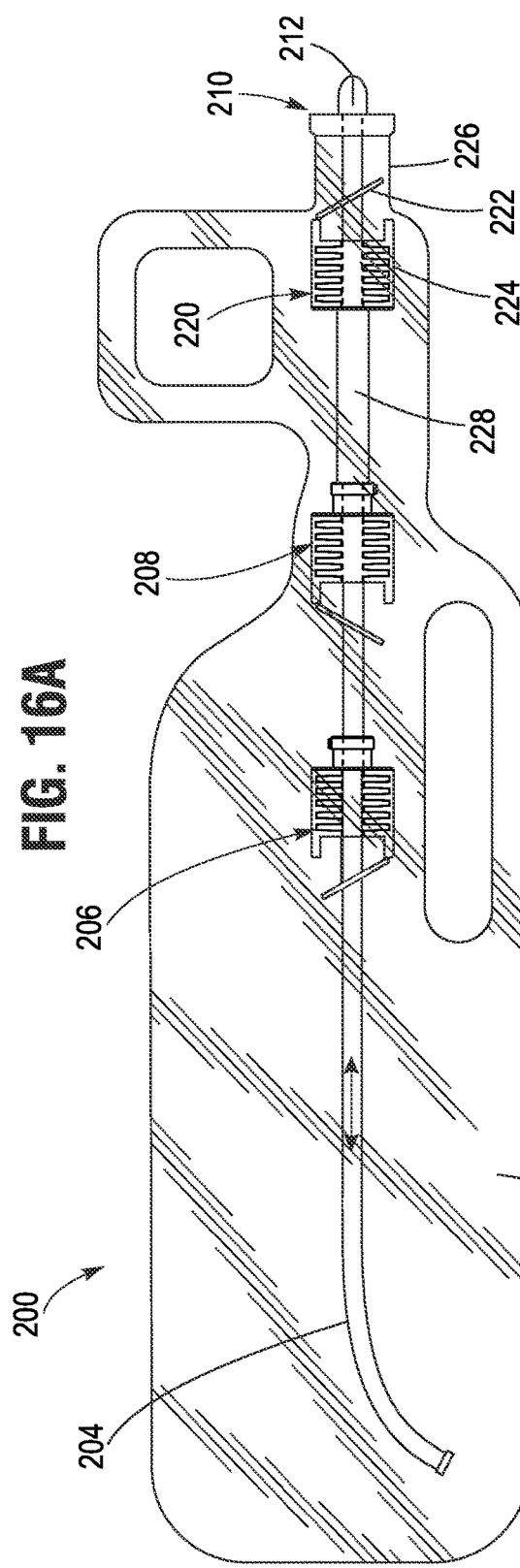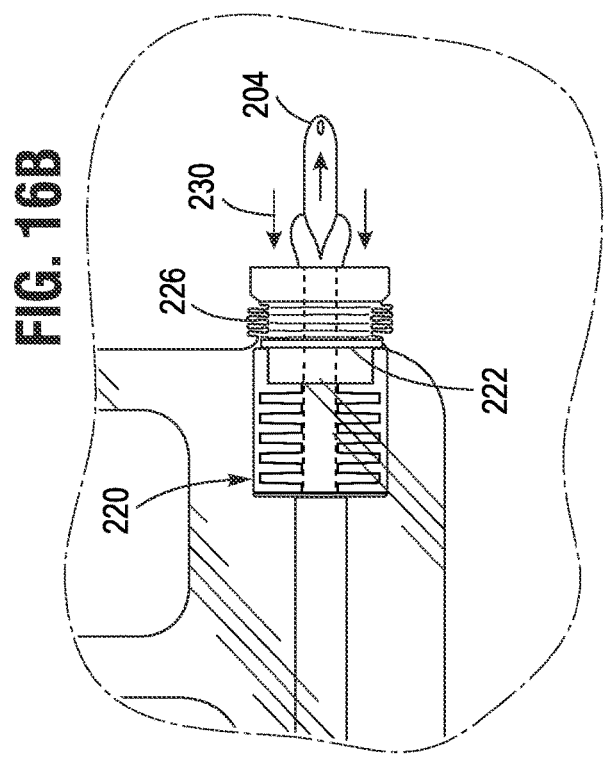

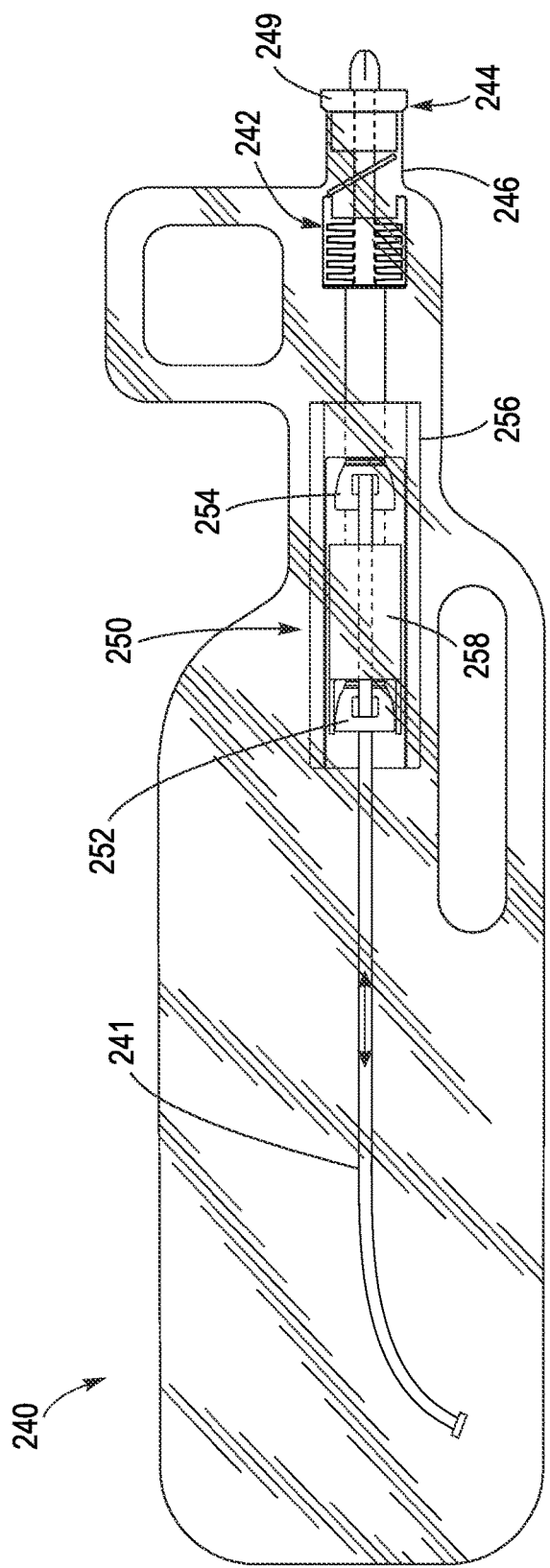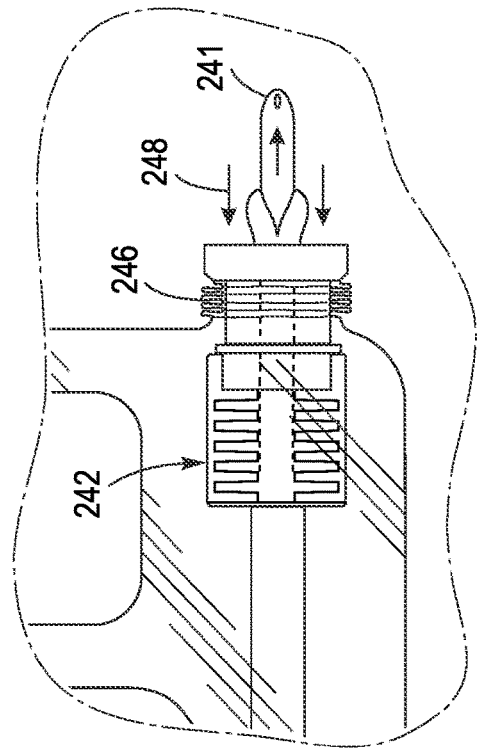
FIG. 17A
FIG. 17B

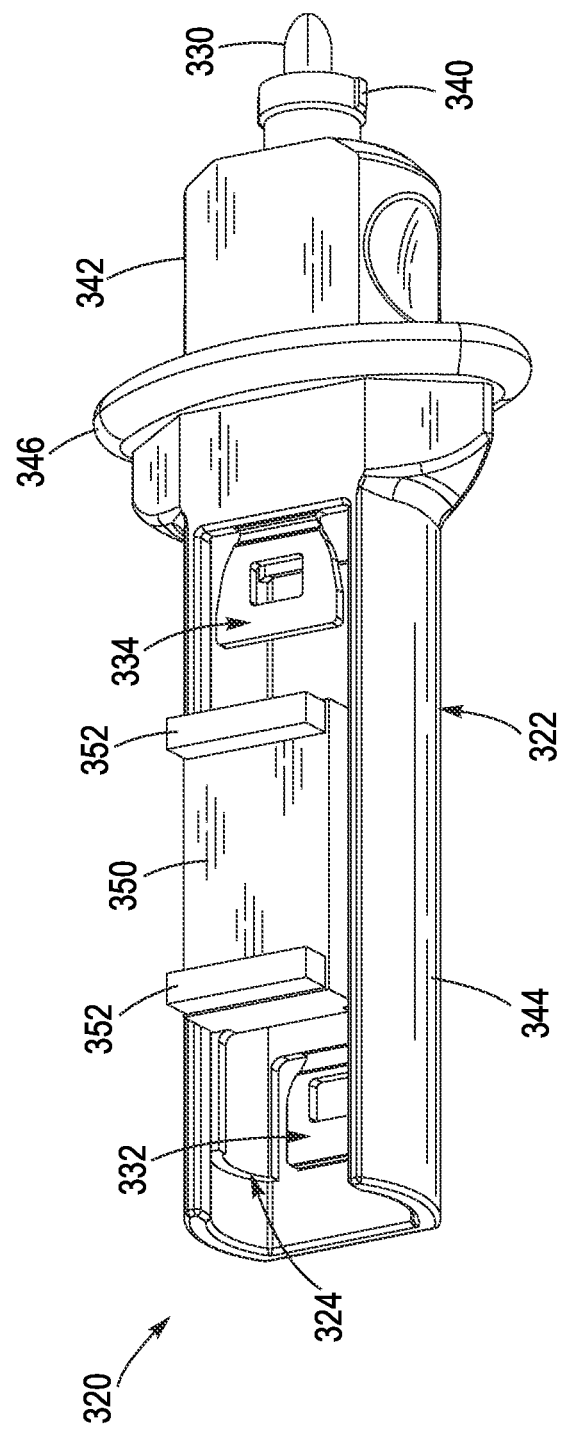

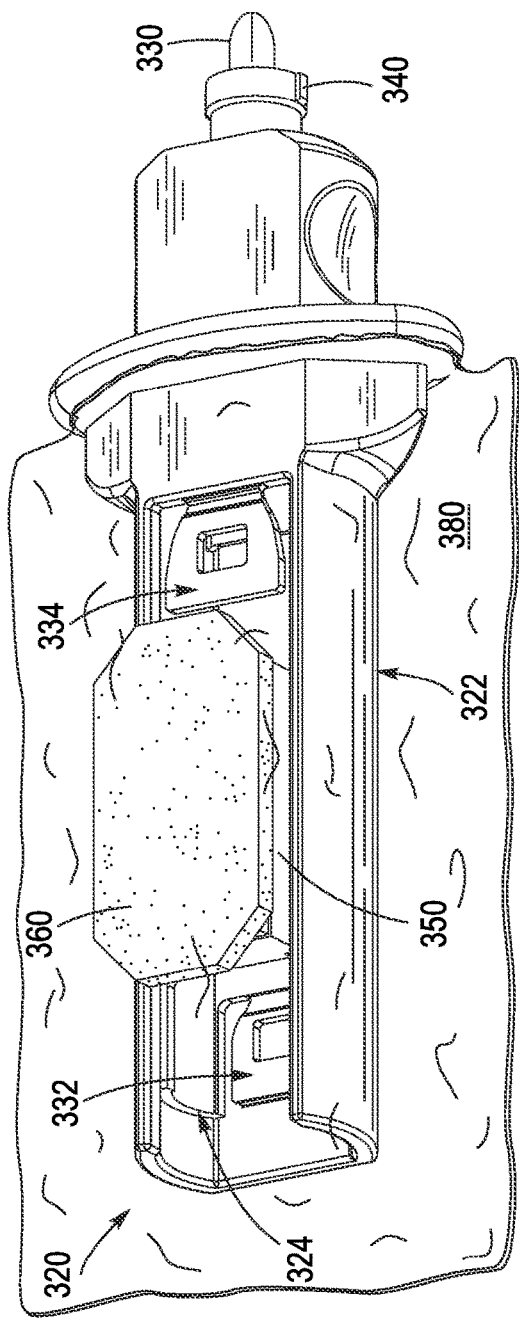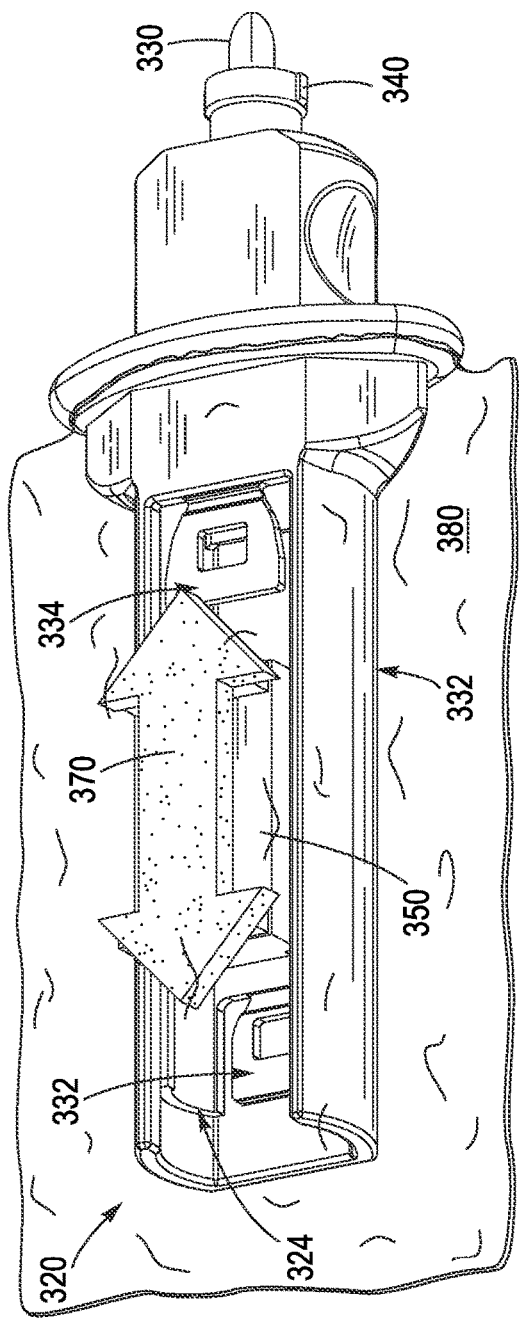

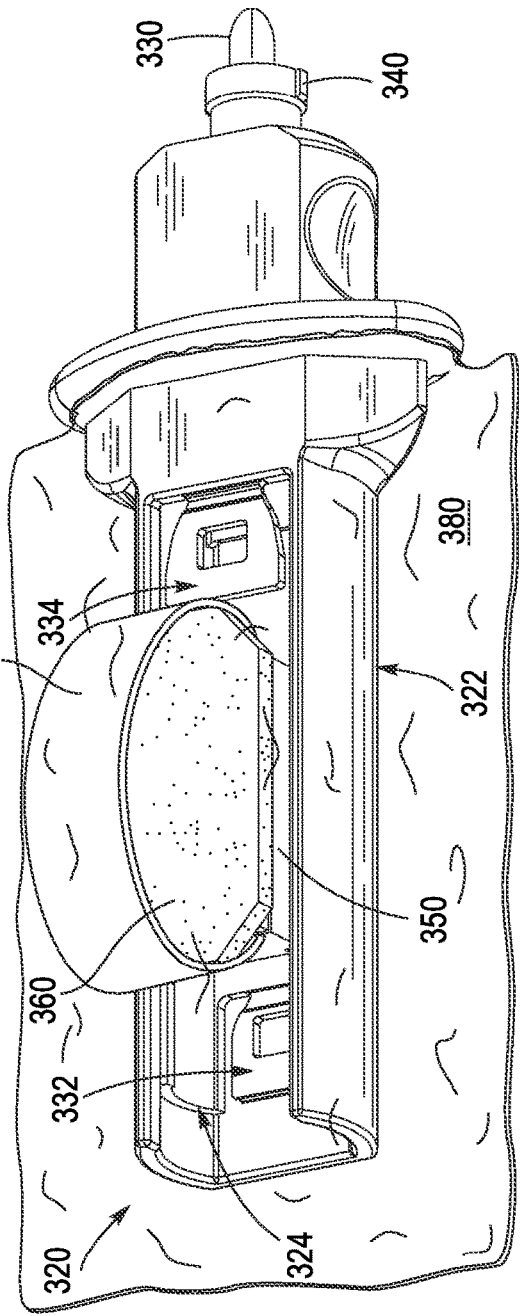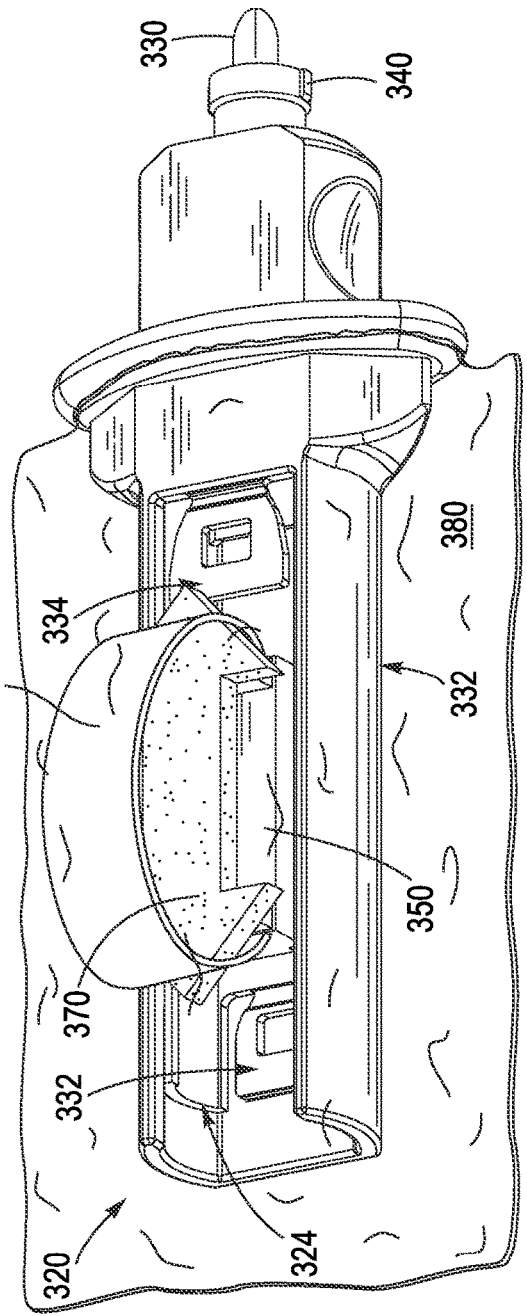

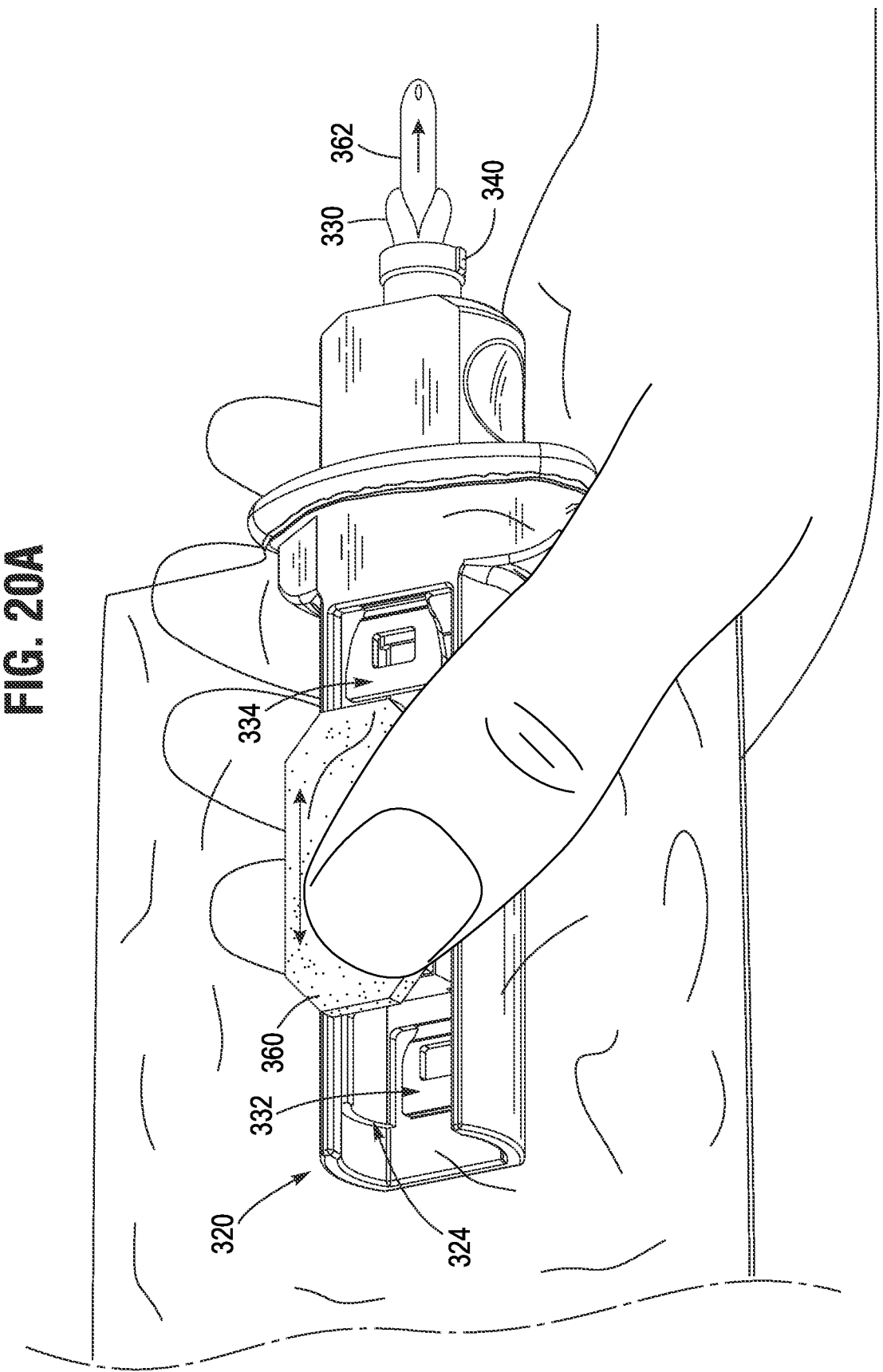

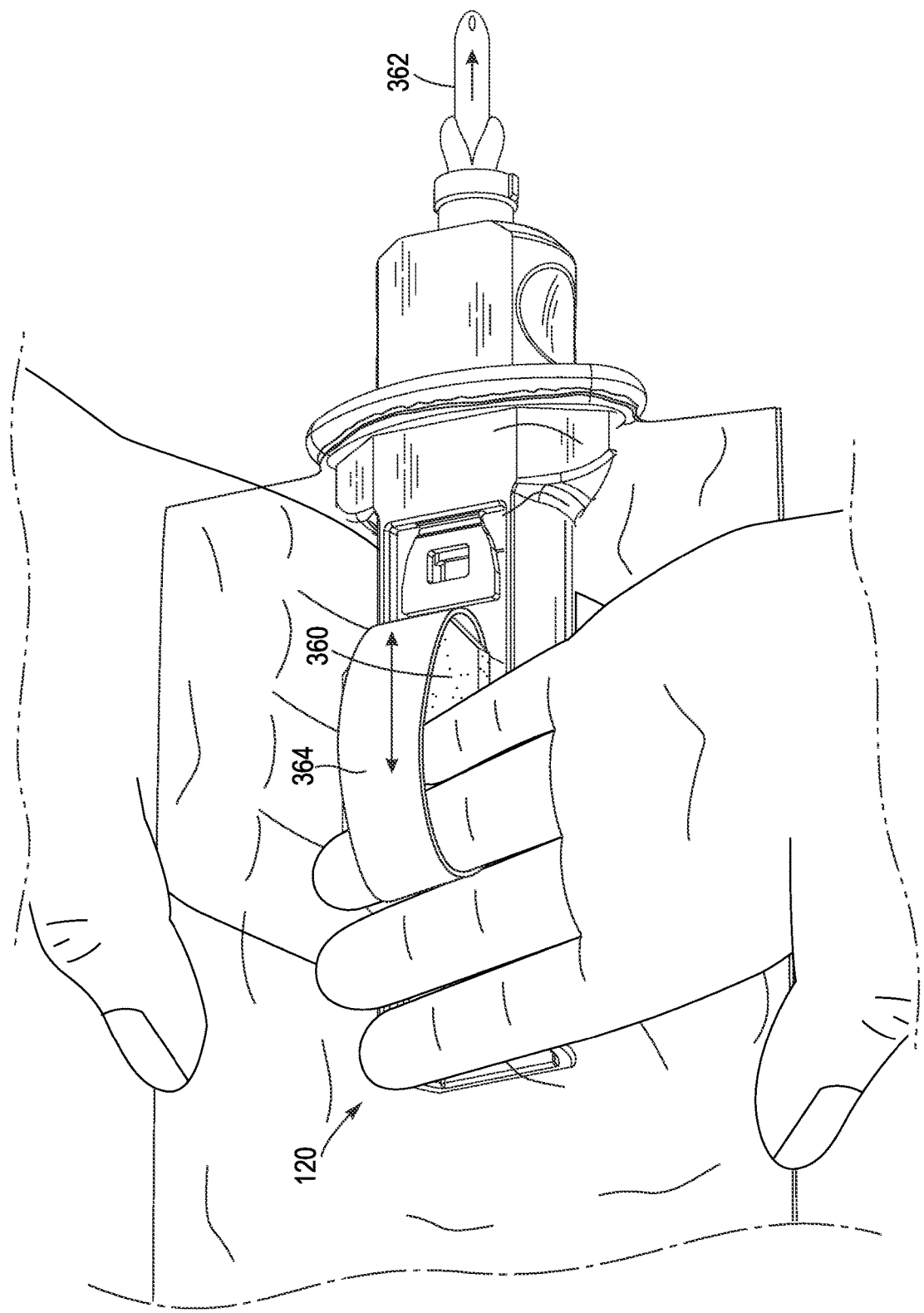

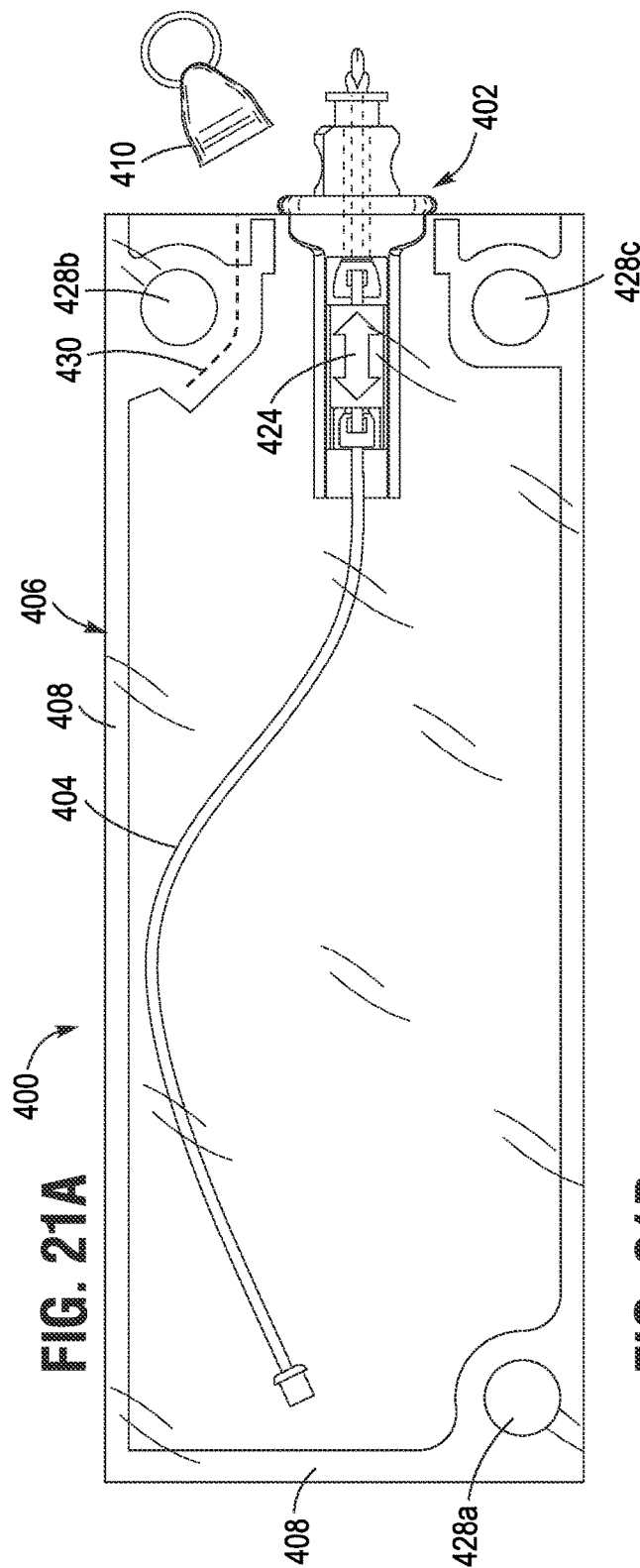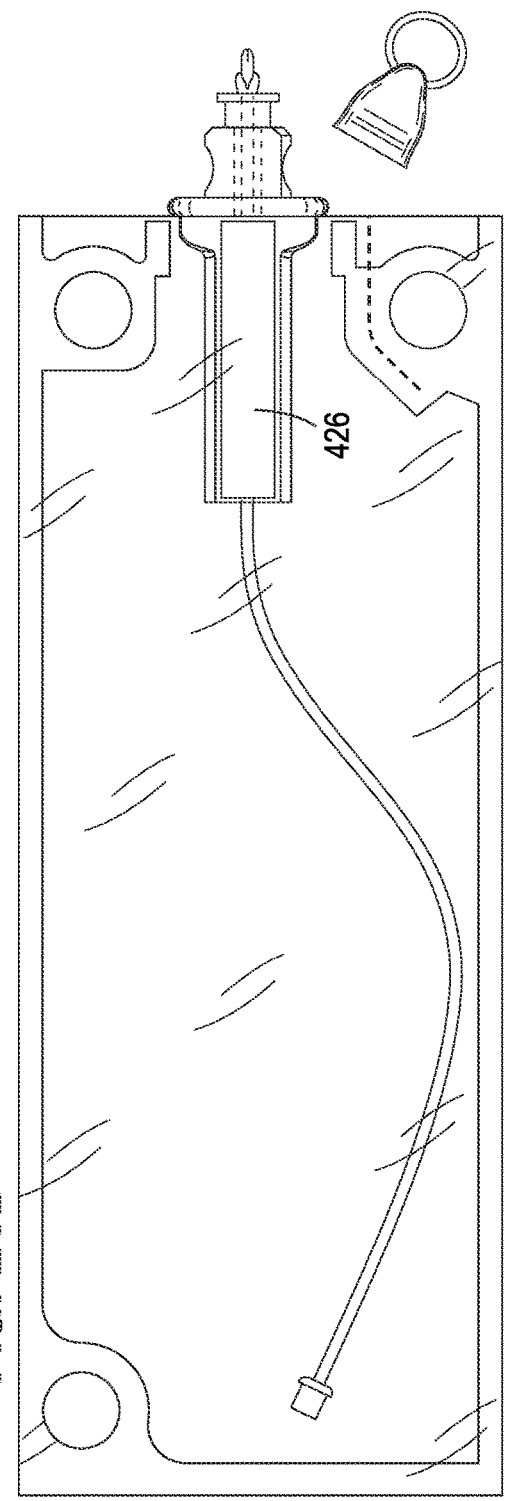

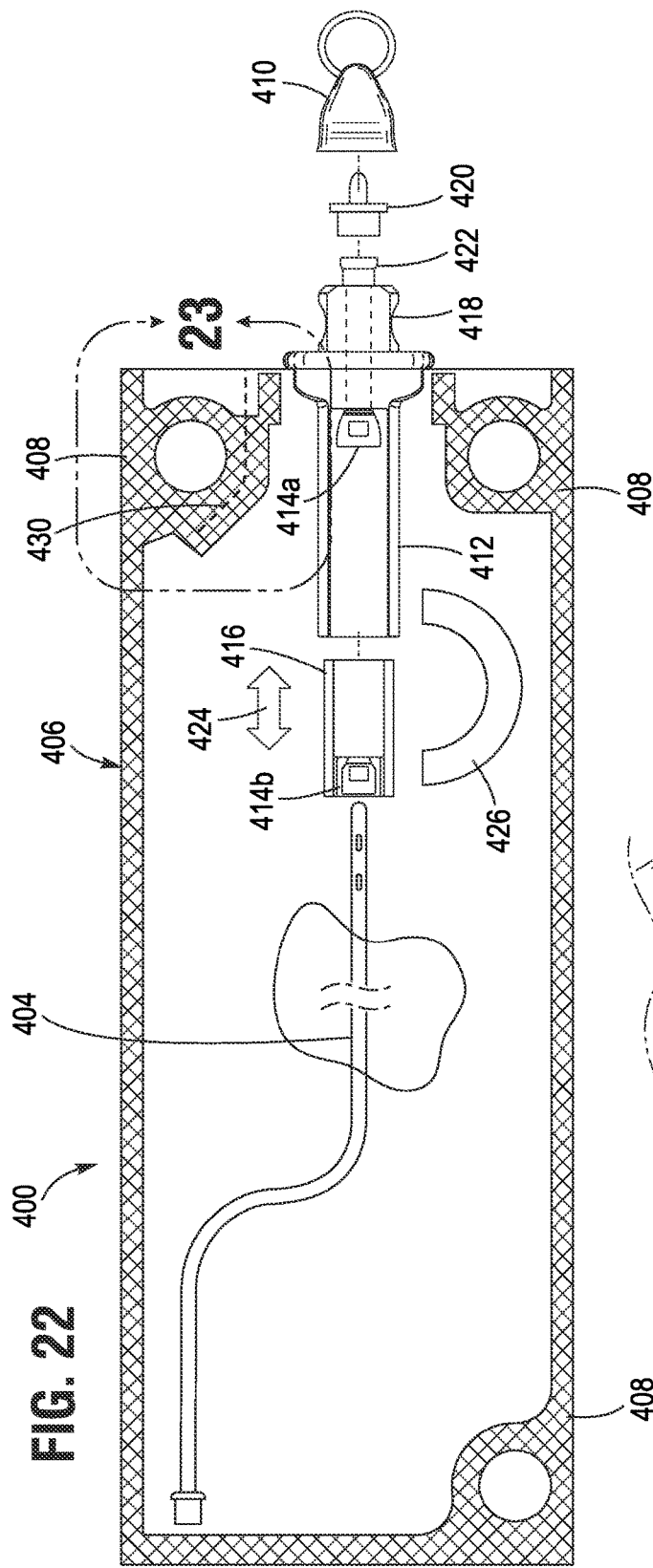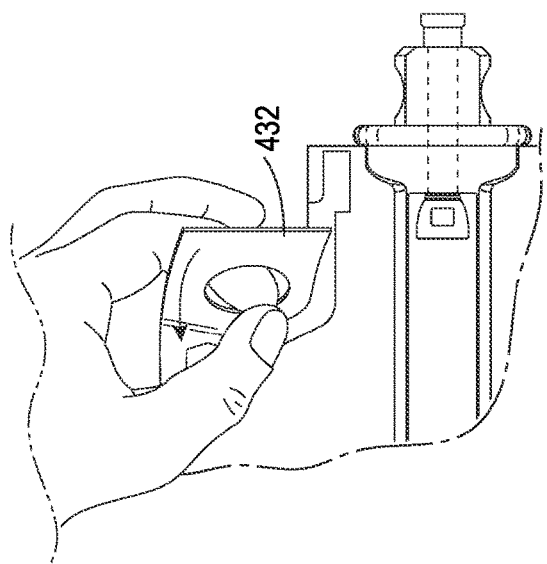
FIG. 22
FIG. 23

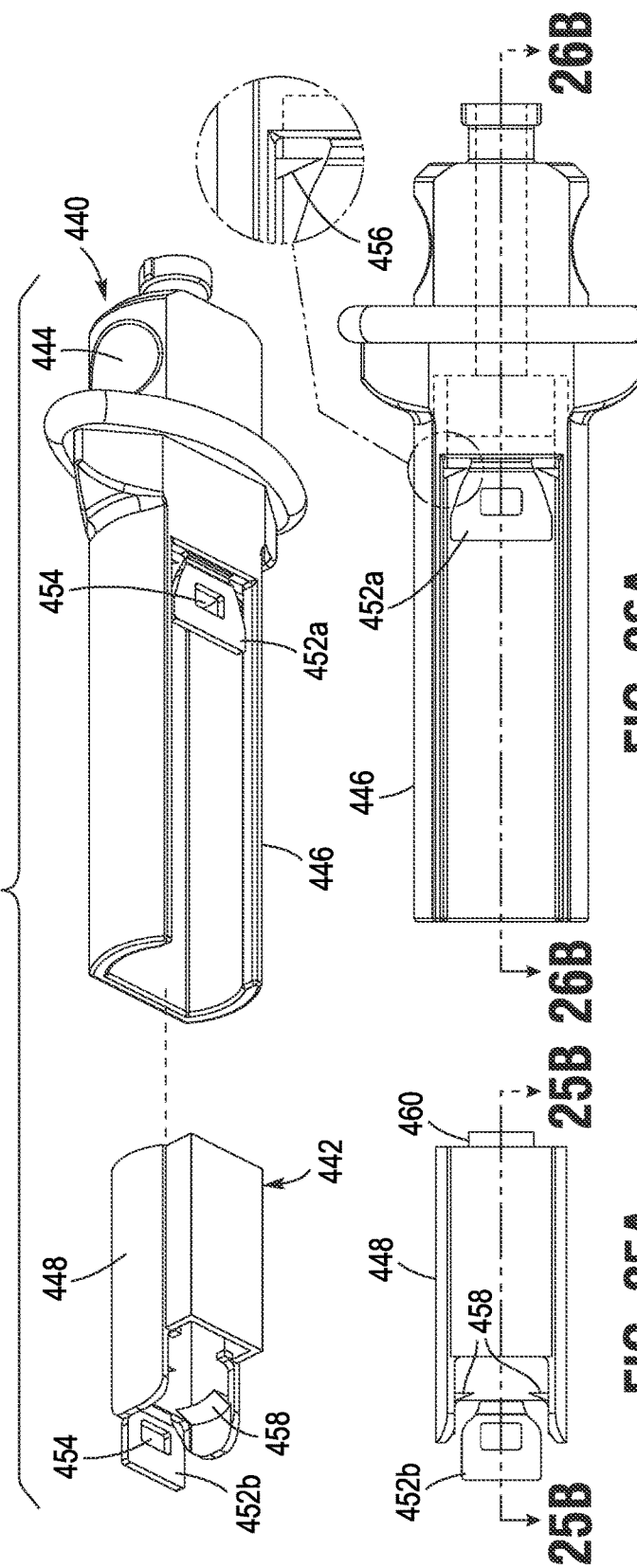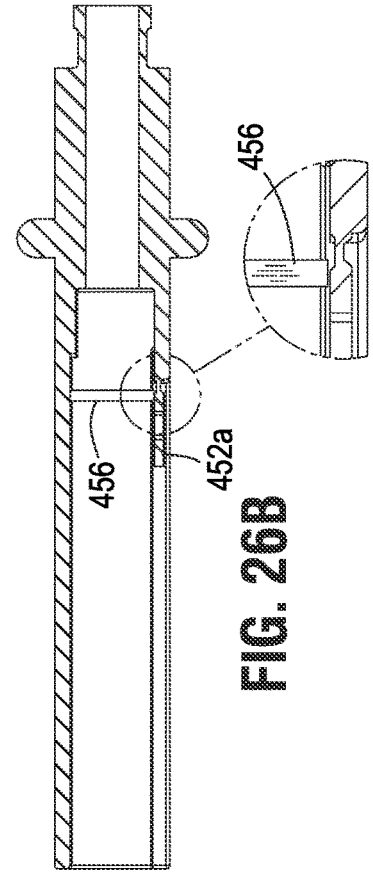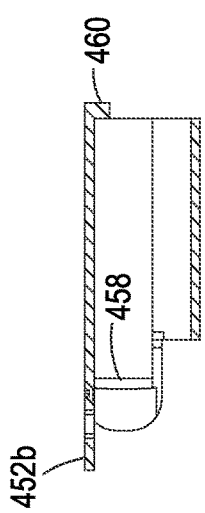

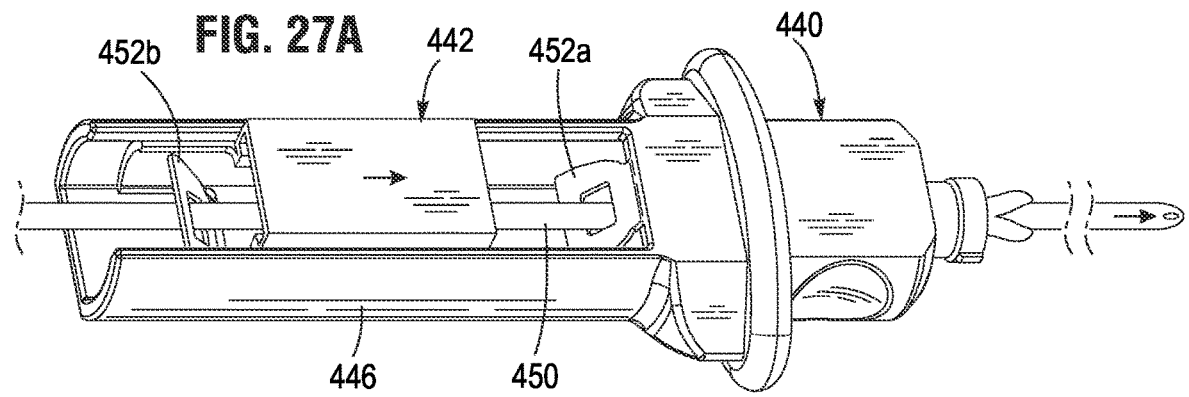
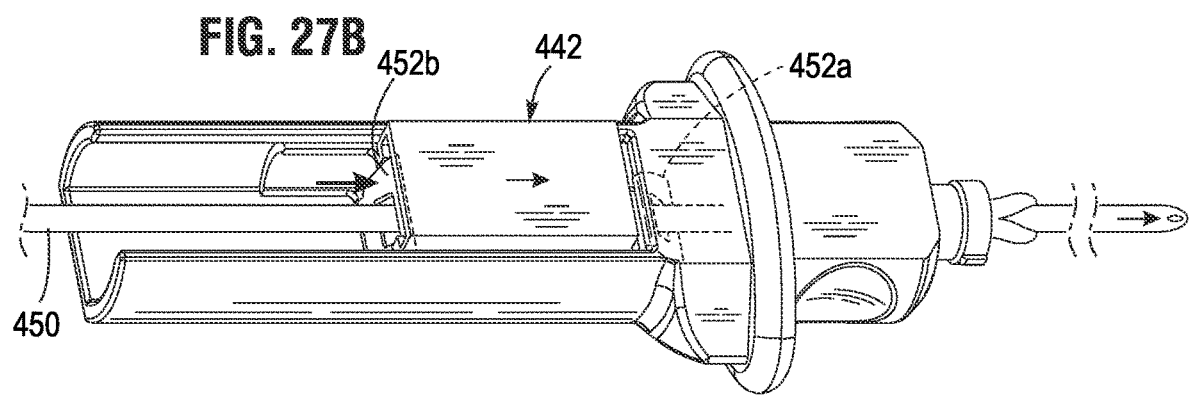
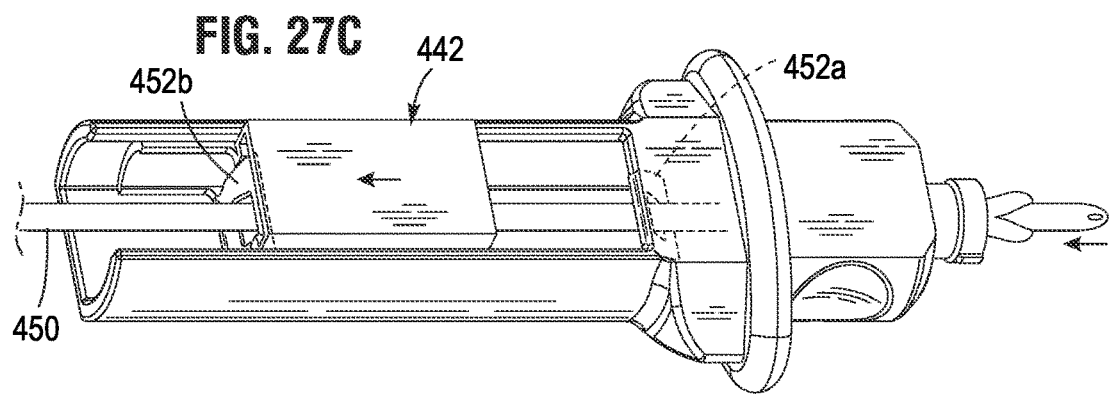

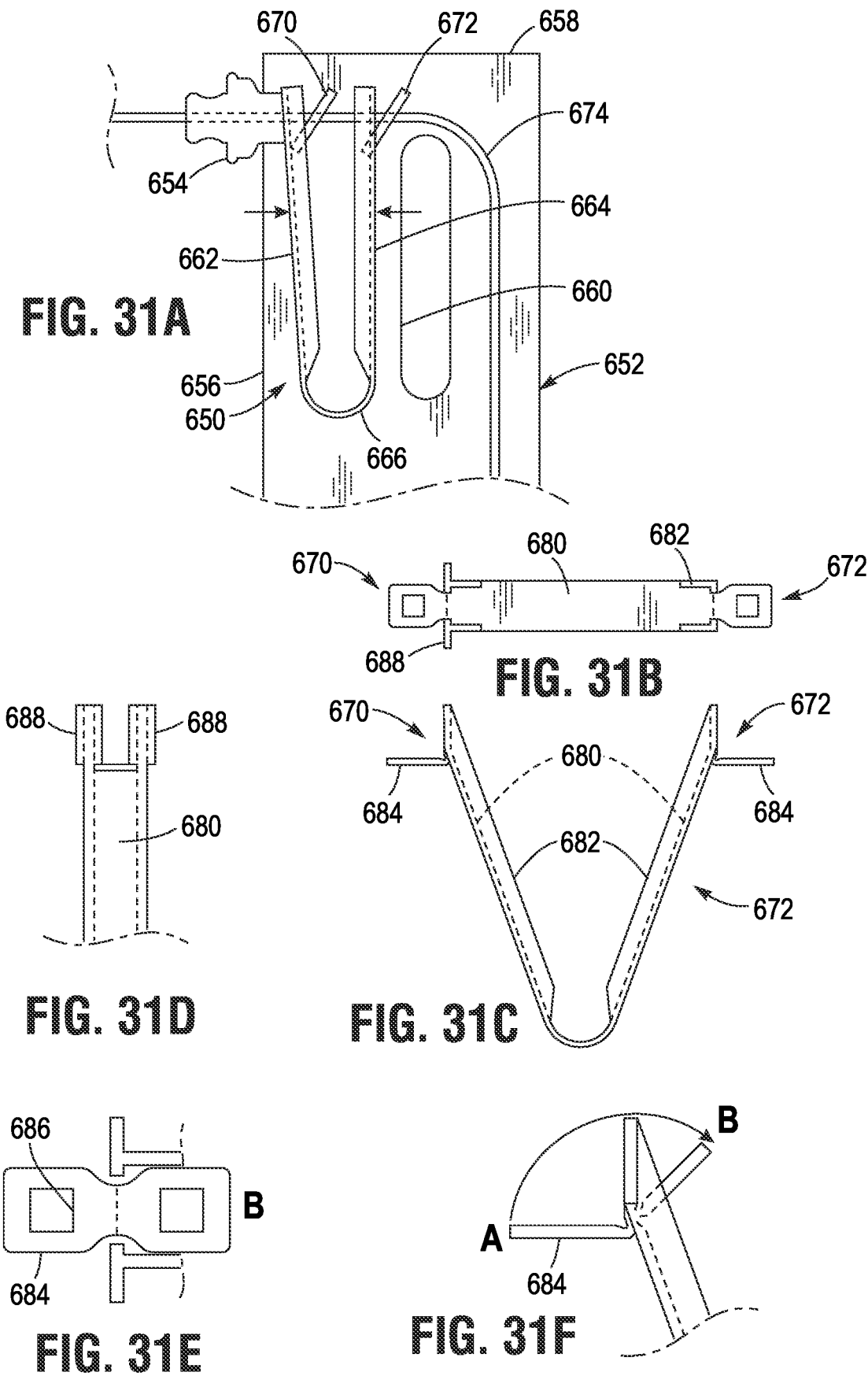

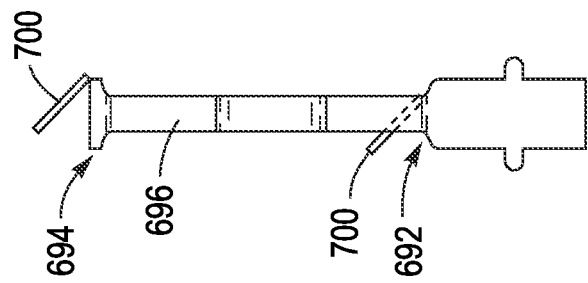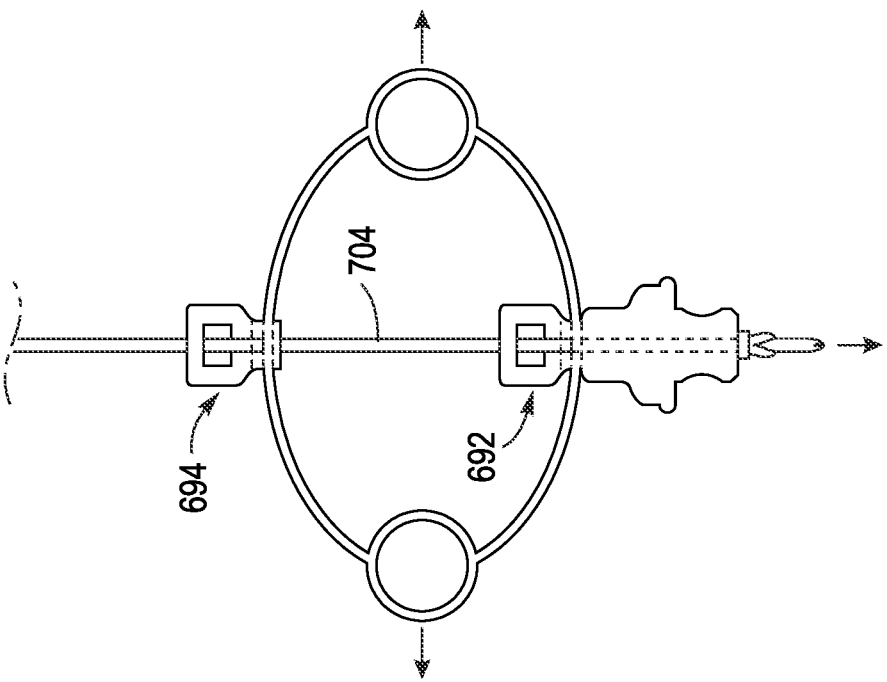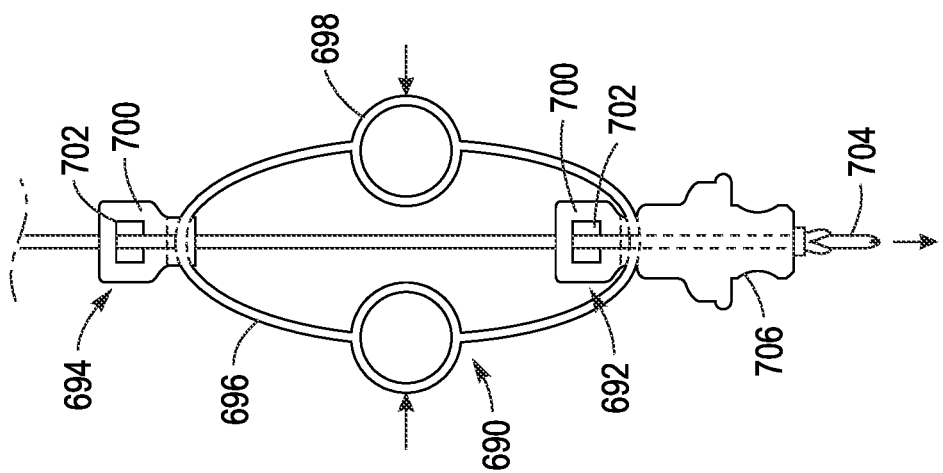

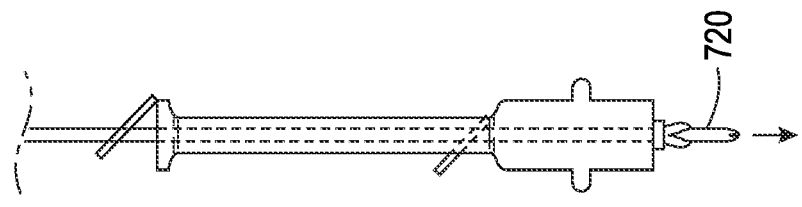
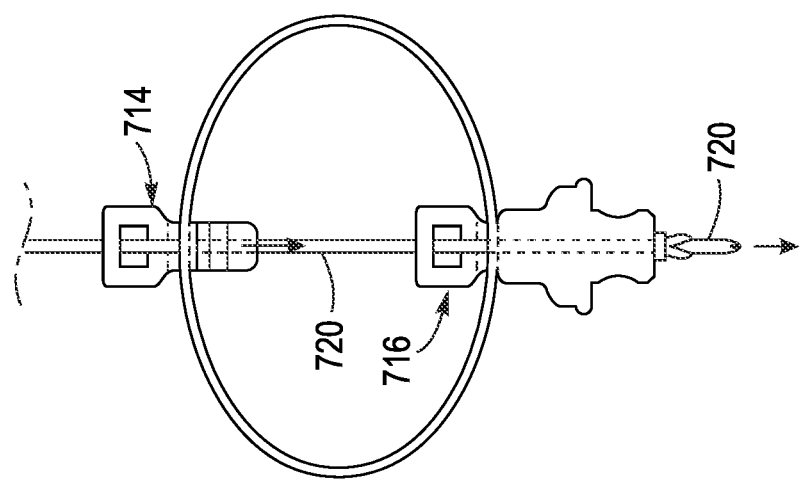
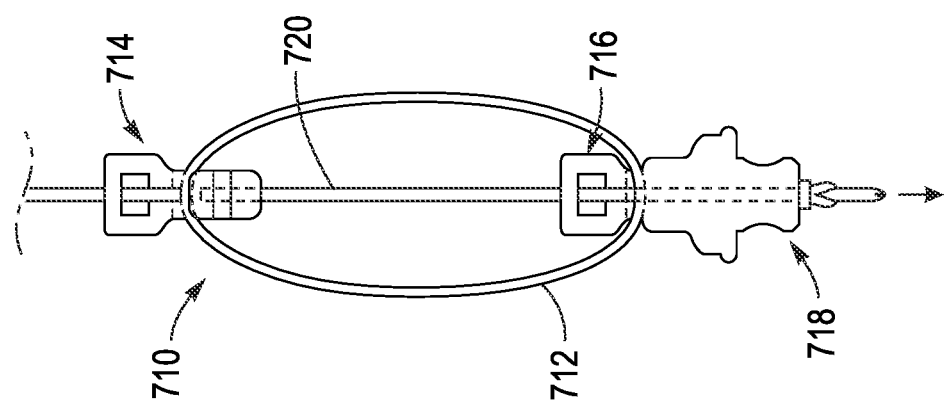

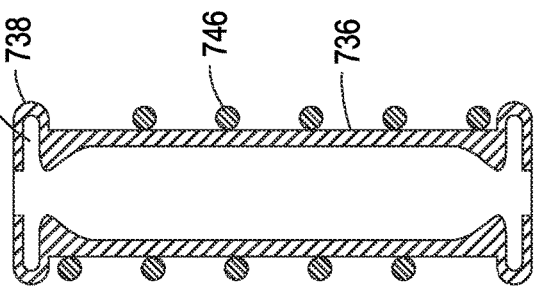
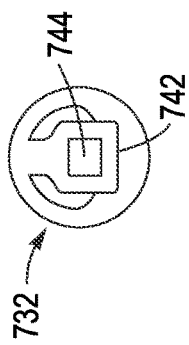
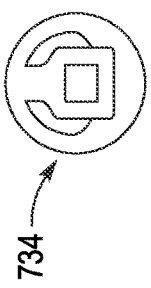
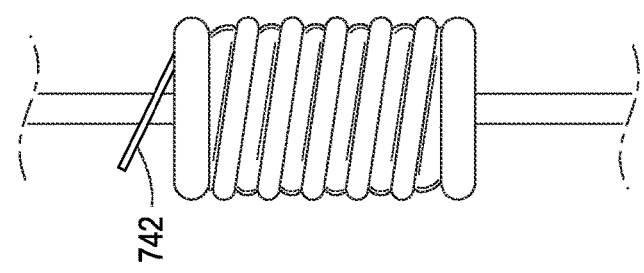
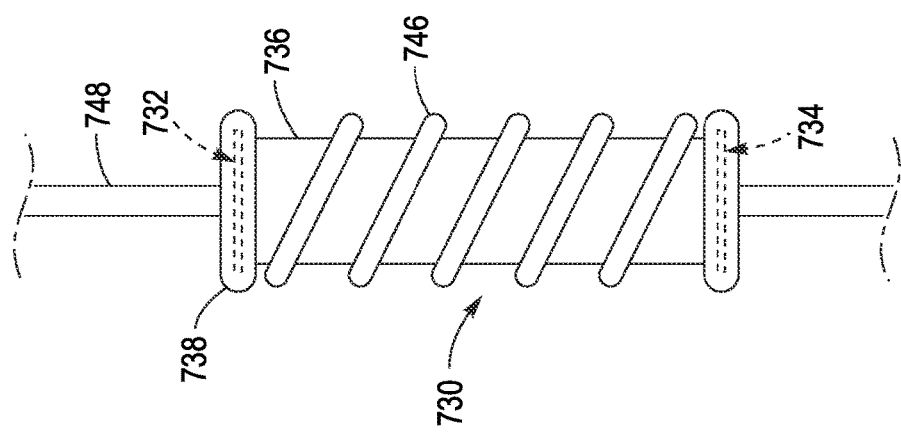

STERILE URINARY CATHETER PACKAGE WITH DISPENSING SYSTEM

RELATED APPLICATIONS

The present application is a continuation-in-part of patent application Ser. No. 16/428,573, filed May 31, 2019, now U.S. Pat. No. 10,980,974, which is a continuation-in-part of patent application Ser. No. 16/111,779, filed Aug. 24, 2018, now U.S. Pat. No. 10,315,008, which is a continuation-in-part of patent application Ser. No. 15/671,341, filed Aug. 8, 2017, now U.S. Pat. No. 10,814,097, the contents of which are expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present application relates to coordinated control devices within a sterile closed intermittent urinary catheter system that facilitate gripping and dispensing of a catheter therein.

BACKGROUND

People with neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. But such continuous catheterization can lead to problems like urinary tract infections (UTI), urethral strictures or male infertility. Intermittent catheterization at regular intervals avoids such negative effects of continuous long term catheterization. Research has shown that intermittent self-catheterization helps reduce urinary tract infections, control urinary leakage (incontinence) and prevent urinary tract damage.

In our highly mobile culture, the ability to have the freedom to leave home for the day or longer is an important part of life. To accommodate this need single use catheters have been developed to allow patients to perform self-catheterization. Urinary catheters are often lubricated to aid in the insertion into a body cavity, thus making the handling of the catheter difficult and messy. Many catheter packages are now designed with the catheter retained in the package. This allows the user to use the package to manipulate the catheter and avoid the messy and possible unsanitary direct contact with the catheter. For instance, a closed system catheter is a self-contained, sterile, pre-lubricated catheter typically housed within a collection bag which eliminates the need to void the urine into a receptacle or toilet as well as the need to hook up any other kind of bag or container. The closed system is also critical for a sterile intermittent catheter insertion technique whereby the catheter is inserted without human touch. However, manipulating a slippery catheter through a plastic bag can be quite difficult even for someone with excellent dexterity. To aid in the manipulation of the catheter various devices have been conceived to assist in movement of the catheter into and out of its package.

For example, U.S. Pat. No. 9,782,563 to Palmer discloses a package including a bag housing a catheter. The catheter passes through a movement control device retained within a housing at the opening of the bag that allows passage of the catheter out of the bag but resists passage back into the bag. Dispensing of a catheter requires the user to hold the movement control device with one hand while using the other hand to grip the lubricated catheter through the bag, typically by pinching the catheter with the thumb and index finger, and pushing the catheter towards and through the movement control device. The one-way valve function of the movement control device thus aids in dispensing of the catheter. Nevertheless, gripping and pushing of a lubricated catheter through the bag is challenging, particularly so for the elderly and the infirm who are the very people who tend to use urinary catheters.

Accordingly, a substantial need continues to exist for a device capable of facilitating and simplifying dispensing of a sterile closed intermittent urinary catheter.

SUMMARY OF THE INVENTION

The present application discloses a sterile closed intermittent urinary catheter system which is an easier to use by virtue of coordinated control devices within the system that facilitates gripping and advancement of a catheter therein.

A first aspect of the application is a packaged catheter equipped with a dispensing system. A first embodiment of the first aspect includes (i) packaging defining a product retention chamber, (ii) a catheter defining a longitudinal axis retained within the product retention chamber, and (iii) a pair of separately translatable movement control devices, each operably engaging the catheter for permitting unidirectional movement of the catheter in a first axial direction relative to the movement control devices.

A second embodiment of the first aspect includes (i) packaging defining a product retention chamber, (ii) a catheter retained within the product retention chamber and defining an insertion end, a fixture end and a longitudinal axis, and (iii) first and second separately translatable movement control devices, each operably engaging the catheter for permitting unidirectional movement of the catheter in a first axial direction relative to the movement control devices, wherein (a) pulling the movement control devices away from one another along the longitudinal axis of the catheter effects longitudinal translation of the first movement control device in a second axial direction opposite the first axial direction along the longitudinal length of the catheter with inconsequential longitudinal translation of the second movement control device along the longitudinal length of the catheter, and (b) pushing the longitudinally separated movement control devices towards one another along the longitudinal axis of the catheter effects longitudinal translation of the second movement control device in the second axial direction along the longitudinal length of the catheter with inconsequential longitudinal translation of the first movement control device along the longitudinal length of the catheter.

The first aspect of the application can optionally be equipped with a handle grip that includes at least (i) a hand-graspable base member fixedly attached to one of the movement control devices, and (ii) a finger-movable member reciprocally engaged to the base member and fixedly attached to the other movement control device, wherein reciprocation of the movable member relative to the base member effects pulling apart and pushing together of the movement control devices along the longitudinal axis of the catheter so as to effect dispensing of the catheter from the packaging.

A second aspect of the application is a method of dispensing a catheter from a packaged catheter in accordance with the first aspect wherein the movement control devices permit unidirectional movement of the catheter in a first axial direction relative to the movement control devices. A first embodiment of the second aspect includes the steps of (i) pulling the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (ii) pushing the longitudinally separated movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, whereby (iii) pushing of the longitudinally separated movement control devices towards one another along the longitudinal axis of the catheter effects dispensing of the catheter out of the packaging. Stated another way, this involves the second movement control device being held stationary against the patient's anatomy while the first movement control device is moved in the first direction to feed the catheter forward. The first movement control device is then moved in the second direction to get another "bite" of the catheter for feed in.

A second embodiment of the second aspect pertains to dispensing a catheter from a packaged catheter in accordance with the first aspect which is equipped with a handle grip, and includes the steps of (i) grasping the base member of the handle grip with a first hand, and (ii) reciprocating the button along a path with a finger on the first hand, wherein (a) movement of the button in one direction along the path effects a pulling movement of the pair of movement control devices away from one another along the longitudinal axis of the catheter so as to effect longitudinal translation of a first movement control device in a second axial direction opposite the first axial direction along the longitudinal length of the catheter with inconsequential longitudinal translation of the second movement control device along the longitudinal length of the catheter, and (b) movement of the button in the other opposite direction along the path effects a pushing movement of the pair of movement control devices towards one another along the longitudinal axis of the catheter so as to effect longitudinal translation of the second movement control device in the second axial direction along the longitudinal length of the catheter with inconsequential longitudinal translation of the first movement control device along the longitudinal length of the catheter, effecting a dispensing of the catheter out of the packaging.

BRIEF DESCRIPTION OF THE DRAWINGS

FIGS. 10A-10C show a pair of movement control devices mounted over a catheter to illustrate a sequence of movement of the catheter using coordinated manipulation of the control members.

FIG. 11 is a plan view of an integrated assembly of a pair of movement control devices mounted within a handle grip component for facilitating single-handed dispensing of the catheter.

FIG. 12 is a perspective view of an integrated assembly of a pair of movement control devices within relatively sliding housings, while

FIG. 16A is a front view of one embodiment of a packaged catheter having a sterile bag and a pair of movement control devices mounted therein for advancing a catheter, and a safety device in the form of a third movement control device mounted near an outlet that prevents premature distal movement of the catheter from the sterile bag, and FIG. 16B is an enlargement of the outlet showing operation of the safety device.

FIG. 17A is a front view of one embodiment of a packaged catheter having a sterile bag and an integrated assembly of a pair of movement control devices mounted therein for advancing a catheter, as well as a safety device in the form of a third movement control device mounted near an outlet that prevents premature distal movement of the catheter from the sterile bag, and FIG. 17B is an enlargement of the outlet showing operation of the safety device.

FIG. 18 is a perspective view of an integrated assembly of a pair of movement control devices within relatively sliding housings having an alternative finger pad.

FIGS. 19A-19D are perspective views of the integrated assembly of FIG. 18 mounted to an outer panel of a sterile bag with alternative friction-enhancing pads and straps in operative relationship with the finger pad.

FIGS. 20A-20D are perspective views of the integrated assembly of FIGS. 19A and 19C mounted to an outer panel of a sterile bag showing a variety of different ways to grasp and reciprocate the finger pad to advance the catheter from within the bag.

FIGS. 21A and 21B are front and rear views of a further embodiment of a packaged catheter in accordance with the present disclosure, depicting an integrated assembly of a pair of movement control members of a dispensing system and a catheter fully retained within the packaging.

FIG. 22 is an exploded assembly view of the packaged catheter of FIG. 21A, and FIG. 23 is an image of one corner of the package being torn away to form a drain.

FIG. 24 is an exploded perspective view of an integrated assembly of a pair of movement control devices within relatively sliding housings, and including structure enabling conversion of the movement control devices for reverse movement of a catheter.

FIGS. 25A/25B and 26A/26B are plan and sectional views through a slider and base, respectively, of the integrated assembly of FIG. 24 illustrating the movement conversion structure.

FIGS. 27A-27C are several steps showing conversion of the integrated assembly of FIG. 24 from forward to reverse movement of the catheter.

FIG. 31A is an assembled view of a squeezable one-piece molded catheter feeder having a pair of movement control devices incorporated within a urine collection bag, and FIGS. 31B-31F are various views of the catheter feeder.

FIGS. 32A and 32B are plan views of an alternative one-piece molded catheter feeder having a pair of movement control devices, and FIG. 32C is a side elevation thereof.

FIGS. 33A and 33B are plan views of a further alternative one-piece molded catheter feeder having a pair of movement control devices, and FIG. 33C is a side elevation thereof.

FIGS. 34A and 34B are plan views of a spring-loaded catheter feeder having a pair of movement control devices inserted therein and shown in expanded and compressed configurations, and FIGS. 34C-34E are sectional and end elevational views of the separate components therein.

DETAILED DESCRIPTION OF A PREFERRED EMBODIMENT

Figure 1:
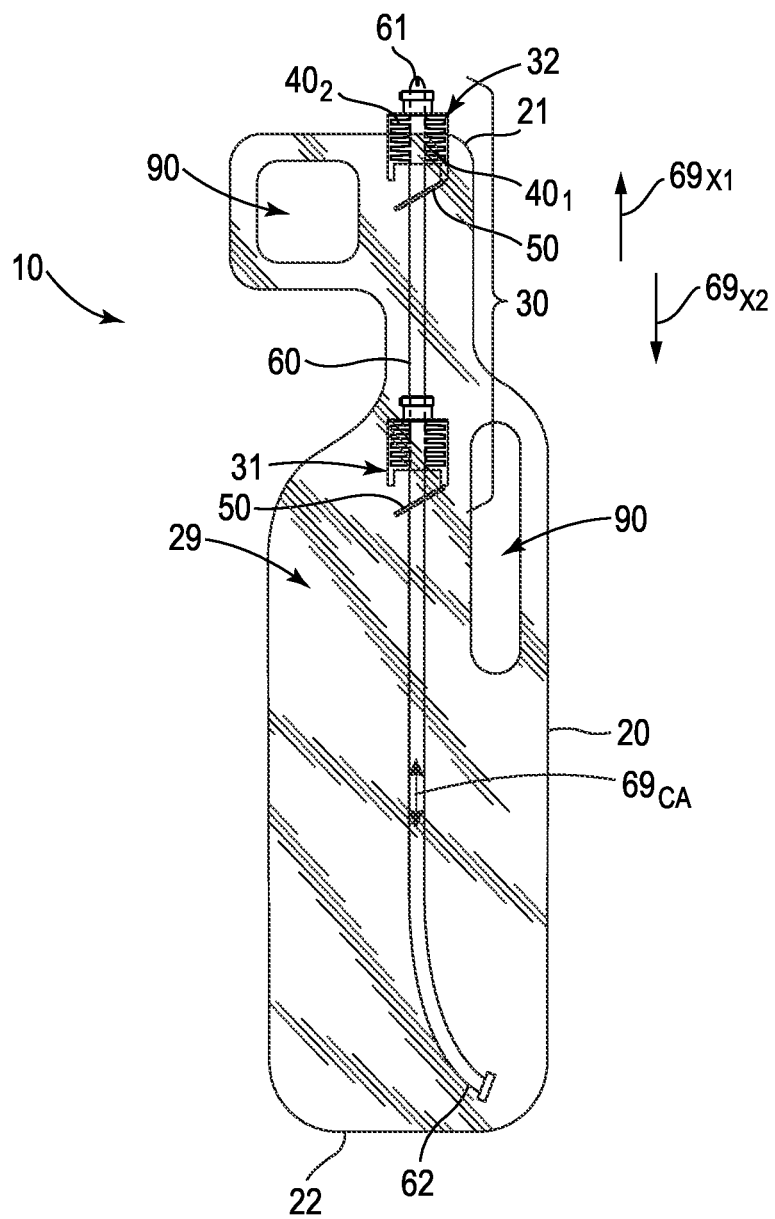
FIG. 1 is a front view of one embodiment of a packaged catheter in accordance with this application, depicting an assembly of a pair of movement control members of a dispensing system pulled apart in a longitudinally spaced relationship and the catheter fully retained within the packaging.

The present application provides a sterile closed intermittent urinary catheter system which is easier to use by virtue of coordinated control devices within a sterile bag that facilitates gripping for advancement and retrieval of the catheter from the collection bag. The catheter is advanced by hand through manipulation from outside the sterile bag.

NOMENCLATURE

10 Packaged Catheter
20 Packaging
21 First Longitudinal End of Packaging
22 Second Longitudinal End of Packaging
29 Product Retention Chamber
30 Dispensing System
31 First Movement Control Device
32 Second Movement Control Device
40 Main Body of Each Movement Control Device
401 First Portion of Main Body of Each Movement Control Device
402 Second Portion of Main Body of Each Movement Control Device
40LA Longitudinal Axis of Main Body
41 First Longitudinal End of Main Body
42 Second Longitudinal End of Main Body
43 Engagement Members
431 First Longitudinally Extending Engagement Member
432 Second Longitudinally Extending Engagement Member
45 Cap or Seal snap fit on the Main Body to hold the soft silicone introducer tip in place at the exit
49 Passageway Through Main Body
49i Interior End (Opening) of Passageway Through Main Body
49e Exterior End (Opening) of Passageway Through Main Body
49CA Central Axis of Passageway
50 Locking Member of Each Movement Control Device
51 First or One Lateral End of Locking Member
52 Second or Other Lateral End of Locking Member
55 Hinge
55P Hinge Pivot Axis
59 Orifice Though Locking Member
59CA Central Axis of Orifice
60 Catheter
61 Lumen or Insertion End
62 Funnel or Fixture End
69CA Longitudinal Central Axis of Catheter
69x1 First Axial Longitudinal Direction
69x2 Second Axial Longitudinal Direction
70 Handle Grip
71 Base Member of Handle Grip
72 Activation Element or Button on Handle Grip
72p Path of Movement of Activation Element or Button
80 Release Actuator Element
90 Handle Opening in Packaging
X Longitudinal Direction
Y Lateral Direction
Z Transverse Direction

Definitions

As utilized herein, including the claims, the term "inconsequential," when used to describe longitudinal translation of a movement control device along the longitudinal length of a catheter, means a distance of less than 1 cm.
Construction Referring to FIGS. 1 and 2, the present application discloses a packaged catheter 10 equipped with a dispensing system 30.
Packaged Catheter The packaged catheter 10 includes a catheter 60, such as an intermittent urinary catheter, retained within the product retention chamber 29 of a package 20. The catheter 60 defines an insertion end 61 and a fixture end 62, and a longitudinal central axis 69CA. Consistent with similar devices, advancement of the catheter 60 into the urethra occurs in a distal direction and retraction in a proximal direction. Therefore, the insertion end 61 is the distal end and the fixture end 62 is the proximal end.

Catheter

The catheter 60 may have any desired longitudinal length and shape effective for achieving the function of eliminating urine from the bladder of a male or female patient. Preferably, the longitudinal length for an adult female catheter 60 is between 2-6 inches, the longitudinal length of the adult male catheter 60 is between 10-16 inches, and the longitudinal length of a pediatric catheter 60 is between 5-11 inches.

Packaging

The packaging 20 may be selected from any of the customary packaging used for catheters so long as the packaging is sufficiently supple and flexible that the packaging 20 does not prevent or inhibit translation of the movement control devices (31 and 32) towards and away from one another when gripped through the packaging 20. In a preferred embodiment, the packaging 20 is in the form of a polymer bag sealed around its exterior edges and around any handle openings therein. The packaging 20 will thus be referred to as a bag from now on, but one of skill in the art will understand that alternative packaging solutions are possible. For instance, the term "bag" implies a closed end, while the packaging used in the catheter system disclosed herein may not be closed, and may instead define a drain line therethrough.

Dispensing System

The dispensing system 30 includes a pair of movement control devices (31 and 32) for facilitating longitudinal x movement of the catheter 60 from a second longitudinal end 22 of the bag 20 towards a first longitudinal end 21 of the bag 20 for controlled dispensing of the catheter 60 from the bag 20.

The movement control devices (31 and 32) each operably engage the catheter 60 and are separately translatable along the longitudinal central axis 69CA of the catheter 60 to cause unidirectional movement of the catheter 60 in a first axial direction 69x1 (distally) relative to the movement control devices (31 and 32). More particularly, and as will be explained below, each movement control device (31 and 32) is constructed so as to automatically be able to freely slide along the longitudinal length of the catheter 60 in a second axial direction 69x2, but is automatically unable to freely slide along the catheter 60 in the first axial direction 69x1.

The unidirectional nature of the movement control devices (31 and 32), allows a user to quickly, easily and controllably dispense a catheter 60 from a bag 20 by repetitively pushing together and pulling apart the paired set of movement control devices (31 and 32). In a preferred embodiment, an outer movement control device 32 is secured to the first longitudinal end 21 of the bag 20 and may be partially exposed out of the first longitudinal end 21, while the inner movement control device 31 is contained within the bag 20. In the configuration of FIG. 1, the inner movement control device 31 is spaced apart from the outer movement control device 32, while in FIG. 2 the inner movement control device 31 has been pushed towards the outer movement control device 32. The catheter 60 is pushed by the inner movement control device 31 which resists relative movement of the catheter therethrough in the second axial direction 69x2, but the catheter slides easily in the first axial direction 69x1 (distally) through the outer movement control device 32. Subsequently, the inner movement control device 31 may be displaced longitudinally over the catheter 60 in the second axial direction 69x2 (proximally) and away from the outer movement control device 32, back into the position shown in FIG. 1.

To summarize, pushing the longitudinally separated movement control devices (31 and 32) towards one another along the catheter 60 effects longitudinal translation of the second movement control device 32 in the second axial direction 69x2 with inconsequential longitudinal translation of the first movement control device 31 along the catheter 60. Conversely, pulling the movement control devices (31 and 32) away from one another along the longitudinal length of the catheter 60 effects longitudinal translation of the first movement control device 31 along the catheter 60 in the second axial direction 69x2 with inconsequential longitudinal translation of the second movement control device 32 along the catheter 60. Stated another way, displacing the inner movement control device 31 in a distal direction relative to the second movement control device 32 advances the catheter 60, and retracting the inner movement control device 31 in a proximal direction relative to the second movement control device 32 resets the inner control device 31 to its initial position without moving the catheter 60.

A further explanation and illustration of the coordinated manipulation of a paired set of movement control devices is provided below in the context of FIGS. 10A-10C.

Movement Control Device

FIGS. 1-9, and in particular FIGS. 3-7, depict a preferred embodiment of the movement control devices 31, 32.

This embodiment of the movement control device 31, 32 has a main body 40 and a locking member 50 hingedly attached to the main body 40. The main body 40 and locking member 50 are preferably formed as a monolithic device with the locking member 50 pivoting about a living hinge 55 formed in the single piece device. The locking member 40 may be made from any suitable material, including various plastics such as polyethylene, polypropylene, polyvinyl chloride (PVC), and nylon.

Figure 4:
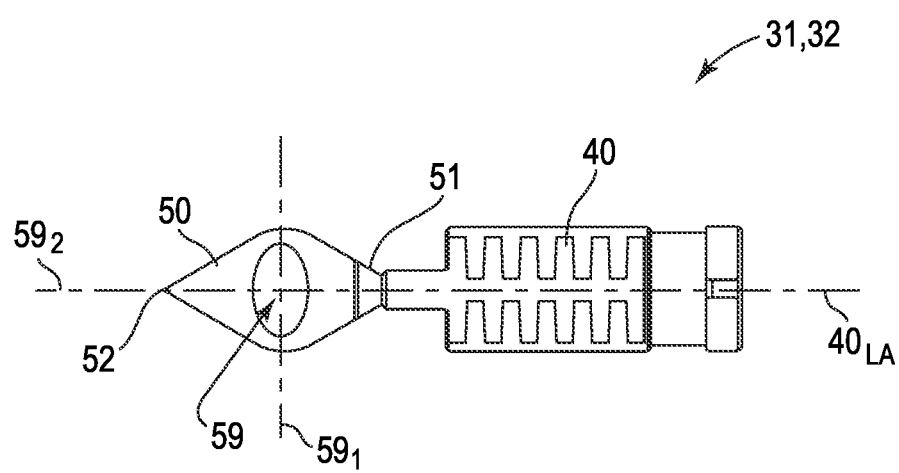
FIG. 4 is a side view of the catheter movement control device depicted in FIG. 3.
Figure 5:
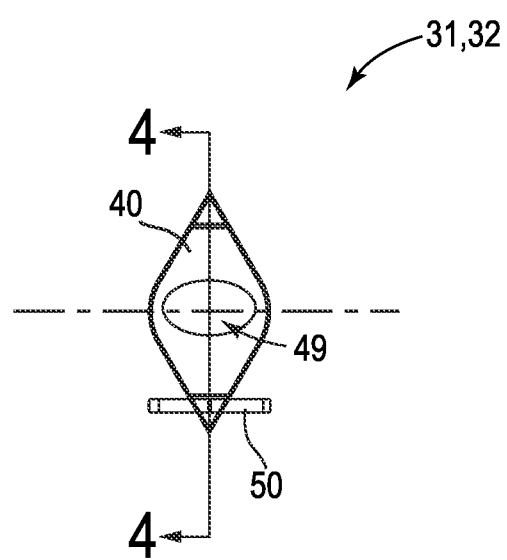
FIG. 5 is an end view of the catheter movement control device depicted in FIG. 3.
Figure 6:
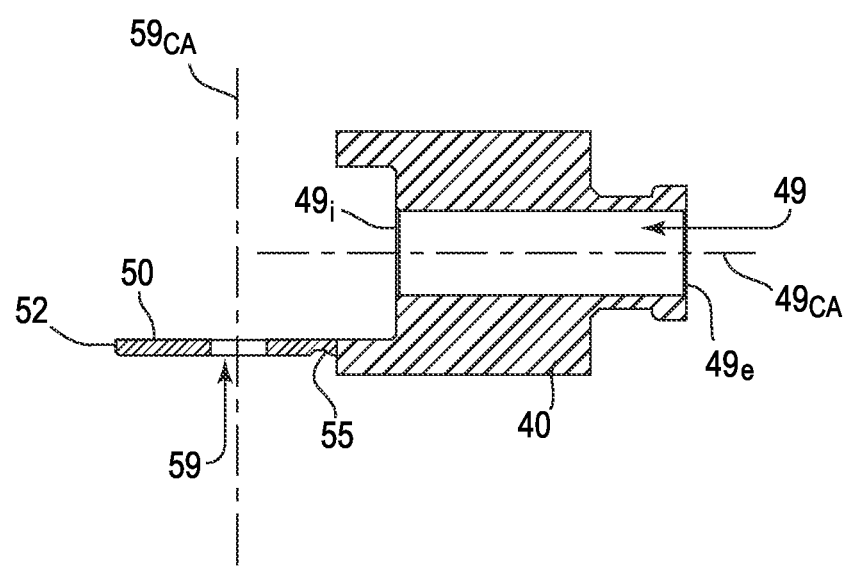
FIG. 6 is a cross-sectional side view of the catheter movement control device depicted in FIG. 3 taken along line 6-6.

The main body 40 of the movement control device 31, 32 has a first longitudinal end 41 and a second longitudinal end 42, and defines a longitudinal axis 40LA (FIG. 4). A passageway 49 extends through the main body 40 from an opening 49i in the first longitudinal end 41 of the main body 40 to an opening 49e in the second longitudinal end 42 of the main body 40. The passageway 49 is preferably linear and defines a central axis 49CA (FIG. 6). The passageway 49 is sized and configured to allow passage of the lumen portion of a catheter 60.

Figure 7:
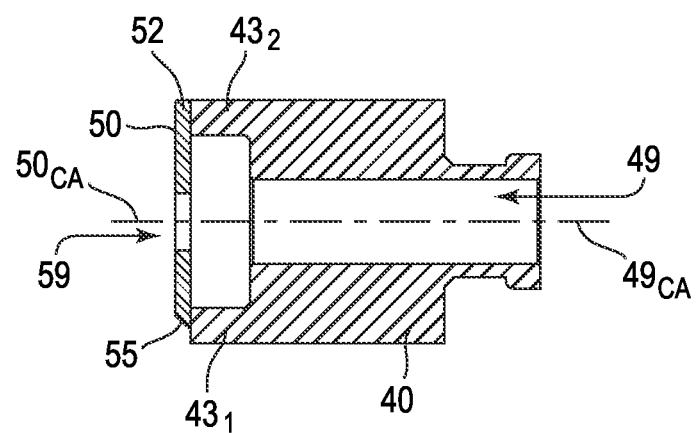
FIG. 7 is a cross-sectional side view of the catheter movement control device depicted in FIG. 3 taken along line 7-7, but with the locking mechanism pivoted into a first dispensing position.

A first lateral end 51 of the locking member 50 hingedly attaches to the main body 40 at hinge 55, permitting pivoting of the locking member 50 relative to the main body 40 about a hinge pivot axis 55p between a first aligned position depicted in FIG. 7, and a second misaligned position depicted in FIGS. 3-6. In the first aligned position the second lateral end 52 of the locking member 50 contacts the main body 40 and the central axis 59CA of an orifice 59 through the locking member 50 is aligned with the central axis 49CA of the passageway 49. When in the first aligned position a catheter 60 may be axially translated through the aligned orifice 59 and passageway 49. Pivoting of the locking member 50 from the first aligned position towards the second misaligned position pivots the second lateral end 52 of the locking member 50 away from the main body 40, resulting in an increasing misalignment of the central axis 59CA of the orifice 59 and the central axis 49CA of the passageway 49 until movement of a catheter 60 is inhibited through the misaligned orifice 59 and passageway 49. Stated another way, friction between the catheter 60 and the orifice 59 pivots the locking member 50 away from the main body 40 into an angled position such that the catheter binds within the orifice 59 and is prevented from moving farther.

In a preferred embodiment, laterally y spaced engagement members 43 extend longitudinally x from a longitudinal end of the main body 40, with a first lateral end 51 of the locking member 50 hingedly attached to a first engagement member 431 at hinge 55, and the second engagement member 432 located to contact the second lateral end 52 of the locking member 50 when the locking member 50 is in the first aligned position. The engagement members 43 provide a modest offset between the passageway 49 and the orifice 59 for avoiding severe bending and kinking of the catheter 60 when the central axis 59CA of the orifice 59 and the central axis 49CA of the passageway 49 are misaligned.

Figure 2:
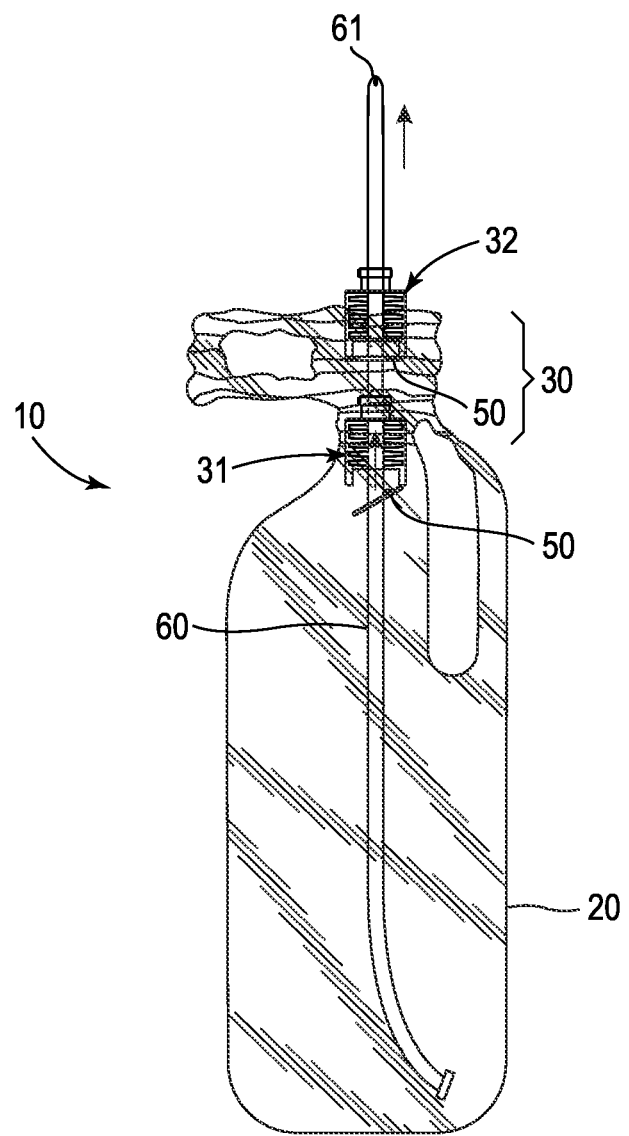
FIG. 2 is a front view of the packaged catheter depicted in FIG. 1 depicting the movement control devices of the dispensing system pushed together and the catheter partially dispensed from the packaging.

Pivoting of the locking member 50 about the hinge pivot axis 55p is effected by axial translation of the movement control device 31, 32 along the longitudinal length of a catheter 60 passing through the passageway 49 and frictionally passing through the orifice 59 in the movement control device 31, 32. Referring generally to FIGS. 1 and 2, axial translation of a movement control device 31, 32 in the first longitudinal direction 69x1 along the length of a catheter 60 causes pivoting of the locking member 50 towards the second misaligned position so as to lock the movement control device 31, 32 onto the catheter 60. When locked, any further movement of the movement control device 31, 32 in the first longitudinal direction 69x1 will effect concomitant movement of the catheter 60 along with the movement control device 31, 32 in the first longitudinal direction 69x1. In other words, the movement control device 31, 32 pushes the catheter 60.

In contrast, axial translation of a movement control device 31, 32 in the second longitudinal direction 69x2 along the length of a catheter 60 causes pivoting of the locking member 50 towards the first aligned position so as to unlock the movement control device 31, 32 from the catheter 60. When unlocked, the movement control device 31, 32 is free to travel along the longitudinal length of the catheter 60. Such freedom of travel can continue along the entire length of the catheter 60 in the second longitudinal direction 69x2, but will of course be promptly lost when the movement control device 31, 32 is moved in the first longitudinal direction 69x1 as the locking member 50 will pivot into the second misaligned position and lock the movement control device 31, 32 onto the catheter 60.

It should be noted that the friction between the catheter 60 and the orifice 59 of each movement control device 31, 32 occurs any time there is relative movement therebetween; i.e., automatically. Therefore, if the catheter 60 slides distally through the orifice 59 it contacts the inner edges of the orifice and causes the locking member 50 to pivot to an aligned unlocked position, whereas when the catheter 60 slides proximally through the orifice 59 it almost immediately causes the locking member 50 to pivot to a misaligned or locked position which binds on the catheter 60. In other words, the catheter 60 may be advanced through each movement control device 31, 32 but cannot be retracted. However, provision may be made to bypass the locking member 50 by including a latch or some other physical impediment to its free movement; such as latching the locking member 50 in an unlocked position. In one example, a release actuator element 80 is shown in and described with respect to FIG. 9.

The size and dimensions of the movement control device 31, 32 are generally dictated by the size of the catheter 60 with which it is used, but the main body 40 should be large enough to be retentively pinched between the thumb and index finger in order to allow dispensing of the catheter 60 from the bag 20 through the movement control device 31, 32. Dimensions of an exemplary movement control device 31, 32 are provided in Table One below.

TABLE ONE (Exemplary Dimensions)

| DIMENSION | SIZE |
| --- | --- |
| Longitudinal Length of Main Body 40 | 25 mm |
| Lateral Width of Main Body 40 | 20 mm |
| Transverse Depth of Main Body 40 | 10 mm |
| Cross Sectional Area of Passageway 49 | 200 mm$^2$ |
| Thickness of Locking Member 50 | 1-2 mm |
| Cross Sectional Area of Orifice 59 | 100 mm$^2$ |

Referring again to FIGS. 1 and 2, at least one of the movement control devices 31 and 32 is preferably fixedly attached to the bag 20 when incorporated into a packaged catheter 10. Namely, a first portion $40_1$ of the main body 40 of the outer movement control device 32 is positioned within the product retention chamber 29 defined by the bag 20, and a second portion $40_2$ of the main body 40 is positioned exterior to the product retention chamber 29. The passageway 49 through the main body 40 of the movement control device 32 provides a port through the bag 20 from an interior end 49i of the passageway 49 to an exterior end 49e of the passageway 49. The affixed movement control device 32 can conveniently be heat sealed at a longitudinal end 21 of the bag 20.

Figure 3:
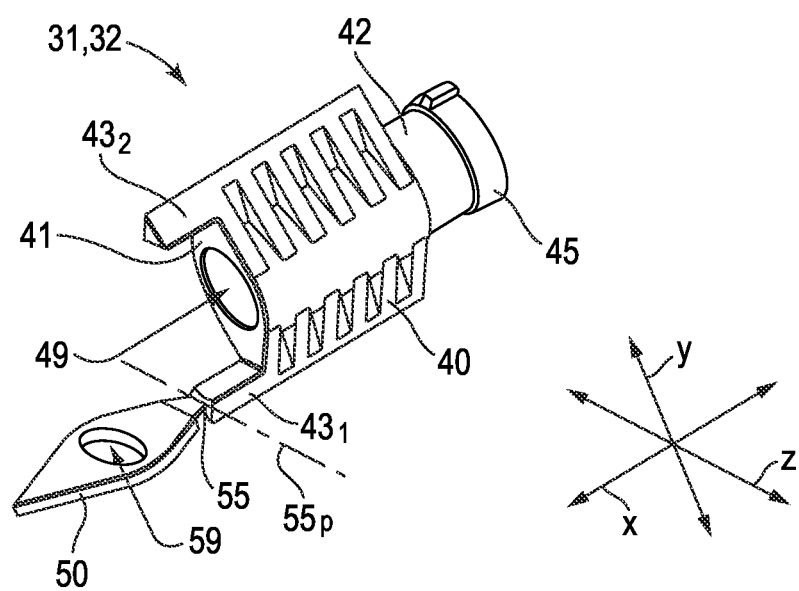
FIG. 3 is a perspective view of one of the movement control devices depicted in FIGS. 1 and 2 with the locking member pivoted into the second locking position.

As seen in FIG. 3, a cap or seal 45 can be placed over the exterior end 49e of the passageway 49 to maintain sterility prior to usage. The inner movement control device 31 is preferably wholly located within the product retention chamber 29 of the bag 20 and may also be fixedly attached to the bag 20 so long as the bag 20 is supple enough to allow the movement control devices 31 and 32 to be pushed together and pulled apart.

Figure 8:
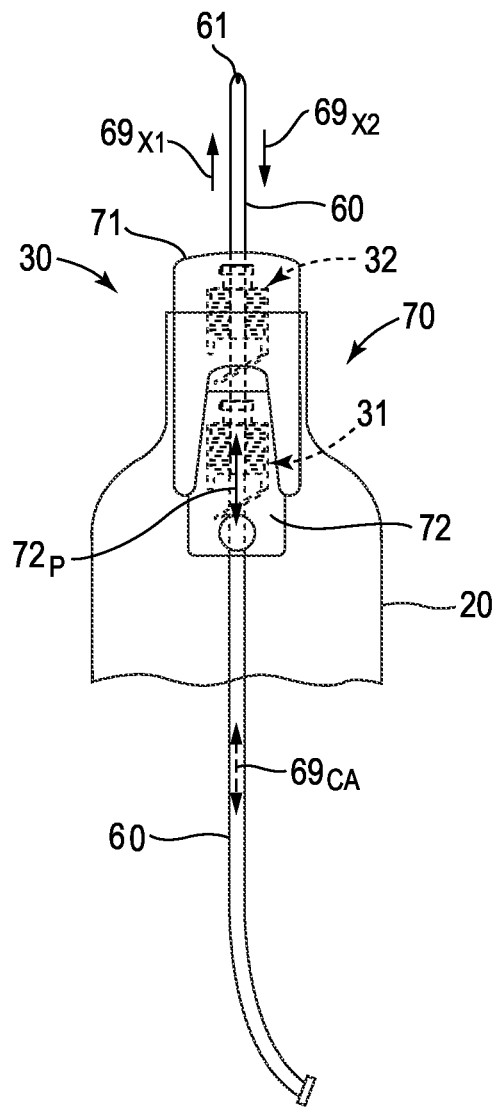
FIG. 8 is a front view of a portion of another embodiment of a packaged catheter schematically depicting a handle grip component for facilitating single-handed dispensing of the catheter.

The dispensing system 30 may further include a handle grip 70 as seen in FIG. 8 for facilitating single-handled dispensing of the catheter 60 from the bag 20 using the dispensing system 30, a feature long sought by users.

FIG. 8 schematically depicts the handle grip 70 having a hand-graspable base member 71, and a finger-movable member 72 reciprocally (i.e., telescopically) engaged to the base member 71 for travel along a path 72p relative to the base member 71. The base member 71 and movable member 72 are preferably sized, configured and arranged for thumb actuation of the movable member 72 while cradling of the base member 71 within the palm of that hand. Of course, the term "finger-movable" implies that the member 72 is movable by a finger, thumb, fist, wrist or any other part of the hand or arm, as well as by using intermediate inanimate objects. The base member 71 is fixedly attached to a second outer one of the movement control devices 32, while the movable member 72 is fixedly attached to a first inner one of the movement control devices 31, whereby reciprocation of the movable member 72 relative to the base member 71 along a path 72p effects a pulling apart and pushing together of the movement control devices 31 and 32 along the longitudinal axis 69CA of the catheter 60 so as to effect dispensing of the catheter 60 from the bag 20.

The finger-movable member 72 may optionally be biased, such as by use of a spring, towards the pushed apart configuration to effect auto "reloading" of the dispensing system 30. When the dispensing system 30 includes a handle grip 70, the bag 20 can be conveniently heat sealed to the base member 71 with the movable member 72 retained wholly within and actuated through the bag 20.

Figure 9:
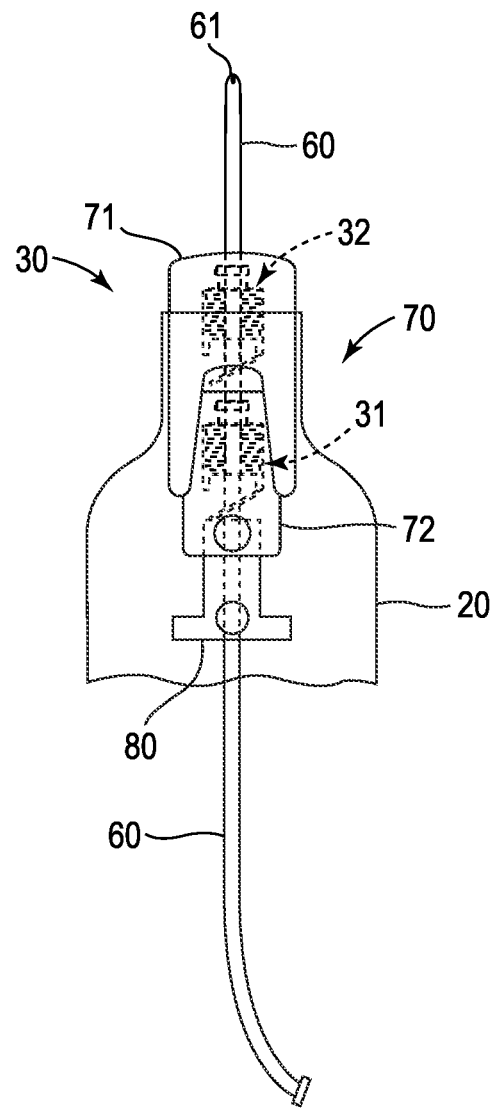
FIG. 9 is a front view of a portion of the handle grip component schematically depicted in FIG. 8, further equipped with a schematically depicted release element.

Referring to FIG. 9, a release actuator element 80 may optionally be provided for effecting selective manual sustained pivoting of the locking member 50 on the first movement control device 31 into the aligned position regardless of real-time longitudinal movement of the catheter 60 relative to the first movement control device 31. This permits movement of a dispensed catheter 60 in the second axial longitudinal direction 69x2 (i.e., retraction) relative to the first movement control device 31. Specifically, actuating the release actuator element 80 while at the same time pushing the first movement control device 31 against the second movement control device 32 to pivot its locking member 50 into the aligned position enables retraction of the catheter 60 back into the bag 20. At the same time, the release actuator element 80 also pushes the first movement control device 31 against the locking member 50 of the second movement control device 32, thus holding the second locking member open to allow free movement through both movement control devices.

The release actuator element 80 may be telescopingly mounted onto the movable member 72 for travel between a first disengaged position and a second engaged position. In the disengaged position, the release actuator element 80 is spaced from the locking member 50 on the first movement control device 31, while in the engaged position the release actuator element 80 contacts and pivots the locking member 50 on the first movement control device 31 into an aligned positioned.

Use

The packaged intermittent urinary catheter 10 can be used by patients for self-catheterization. Prior to use the patient should take all sanitary procedures advised by their doctors to decrease the risks of infection.

Referring to the embodiment depicted in FIGS. 1 and 2, first the seal or cap 45 is removed to open the port through the bag 20 defined by the passageway 49 through the main body 40 of the second movement control device 32.

The user then grasps or pinches the main body 40 of the first or inner movement control device 31 through the bag 20 with one hand, grasps or pinches the main body 40 of the second or outer movement control device 32 with the other hand through the bag 20, and then repetitively pushes together and pulls apart the movement control devices 31 and 32 as depicted in FIGS. 1 and 2. As mentioned, pulling the two movement control devices 31 and 32 apart "loads" the dispensing system 30 without expelling the catheter 60 from the bag 20, and pushing the movement control devices 31 and 32 together dispenses a length of the catheter 60 from the bag 20.

A clearer depiction of this "inchworm" sort of catheter advancement is seen in FIGS. 10A-10C where a first or inner movement control device 101 and a second or outer movement control device 102 are shown mounted over a catheter 104. The first and second movement control devices 101, 102 may be identical to that shown in FIGS. 3-7. By "mounted over" the catheter 104 is meant that the catheter passes through the longitudinal passageway through the main body 110 and the orifice though the locking member 112 of each movement control device 101, 102. A symbolic line 106 is drawn to represent an outer edge of the sterile bag within which the catheter 104 is stored.

FIG. 10A is a resting position with the catheter 104 stored within the sterile bag 106 and preferably inside of a bullet-shaped introducer tip 114 mounted to an exterior end of the outer movement control device 102. The introducer tip 114 is sized to fit within the outer end of the urethra and made of a flexible elastomer which has petals that the catheter 104 spreads apart upon passage therethrough. When the user wishes to utilize the catheter, the bag 106 is first brought into proximity with the genitals, and the introducer tip 114 inserted into the tip of the urethra. The introducer tip 114 helps prevent any bacteria that may be around the urethra opening from contacting the catheter 104, which in turn helps reduce instances of infection.

Next, the user holds the outer movement control device 102 steady through the bag 106 and grasps and advances it toward the inner movement control device 101, as in FIG. 10B. Friction between the catheter 104 and the orifice though the locking member 112 of the inner movement control device 101 pivots the locking member away from the main body 110 to about a 45° angle as shown. This misaligns the orifice though the locking member 112 with the catheter axis and causes the catheter 104 to be pushed along by the inner movement control device 101. The catheter 104 emerges from the petals of the introducer tip 114 into the outer end of the urethra. Friction between the catheter 104 and the orifice though the locking member 112 of the outer movement control device 102 forces the locking member to pivot toward and eventually contact the main body 110, which aligns the orifice though the locking member 112 with the catheter axis and permits catheter movement.

Finally, FIG. 10C shows leftward movement of the inner movement control device 101 over the catheter 104 which pivots its locking member 112 against the main body 110, aligns the orifice though the locking member with the catheter axis and permits movement thereover. The locking member 112 of the outer movement control device 102 is slightly pulled by the catheter 106 to the angled, misaligned position shown, which creates friction on the catheter and prevents it from being retracted farther back into the bag 106. Repeating the steps shown in FIGS. 10B and 10C gradually inches the catheter 104 out of the sterile bag 106 and through the urethra of the user to the desired location where urine flows.

Referring to FIGS. 1 and 2, two-handed pushing and pulling of the movement control devices 31 and 32 to effect dispensing of a catheter 60 may be simplified by attaching both movement control devices 31 and 32 to the bag 20 in longitudinally spaced relationship and providing a handle opening 90 proximate each movement control device 31 and 32.

The dispensing system 30 also functions to prevent the fixture end 62 of the catheter 60 from advancing out of the bag 20.

Referring to the embodiment depicted in FIGS. 8 and 9, the user cradles the base member 71 in the palm of a hand with the fingers wrapped around and gripping the base member 71 and the thumb of that same hand placed upon a pad on the activation element 72. The user then uses the thumb to reciprocate the activation element 72 relative to the base member 71 along the path of travel 72p, thereby pulling the movement control devices 31 and 32 apart and loading the system. Subsequently, pushing the movement control devices 31 and 32 together dispenses a length of the catheter 60 from the bag 20 when the activation element 72 is moved in the opposite direction along the path 72p.

Still referring to FIGS. 8 and 9, one-handed pushing and pulling of the movement control devices 31 and 32 to effect dispensing of a catheter 60 may be simplified by including the handle grip 70 feature.

ALTERNATIVE EMBODIMENTS

In addition to the previously-described movement control devices and handle grips integrating the same, the applicants have developed further alternatives for use in sterile closed intermittent urinary catheter systems, as explained below.

FIG. 11 is a plan view of an integrated assembly 120 of a pair of movement control devices mounted within a handle grip for facilitating single-handed dispensing of the catheter. With specific reference to FIGS. 12-15, the integrated assembly 120 includes a larger base member 122 and a smaller movable member 124 arranged to move within the base member. The base member 122 is desirably secured to one end of a sterile bag, as schematically shown at 126 in FIG. 11, and defines an exterior handle grip of the integrated assembly 120. A catheter 128 passes longitudinally through the assembly 120 and typically is positioned with its distal tip just inside of an introducer tip 130 in a stored position.

Greater detail of the integrated assembly 120 is shown in FIGS. 12-15, but FIG. 11 depicts the sterile bag 126 at the same placement as the sterile bag 106 in FIGS. 10A-10C as well as a pair of movement control devices 132, 134 within the assembly. A first or inner movement control device 132 forms a part of the movable member 124 while a second or outer movement control device 134 forms a part of the base member 122. It will be understood that relative displacement of the movement control devices 132, 134 advances the catheter 128 in the "inchworm" manner depicted in FIGS. 10A-10C.

With reference now to the detailed views of FIGS. 12-15, the larger base member 122 includes a distal hub 140 from which the introducer tip 130 projects. The hub 140 in turn is molded together with an ergonomic external handle 142 and an internal housing 144 which are separated by a flange 146. When assembled with the sterile bag 126, the handle 142 is outside while the housing 144 is inside, with the bag 126 preferably adhered or heat sealed to the interior of the flange 146, as seen in FIG. 11. The integrated assembly 120 has a generally rectangular lateral cross-section which presents a flat non-rotating profile inside the bag to help the user apply pressure from both sides.

Figure 12:
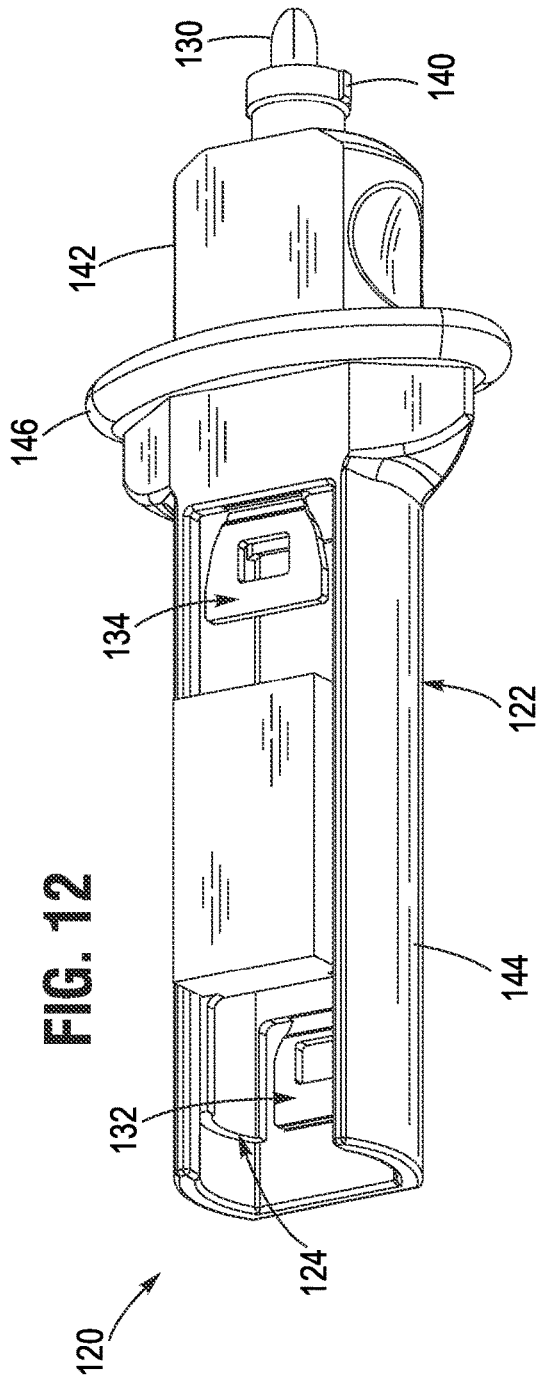
Figure 13:
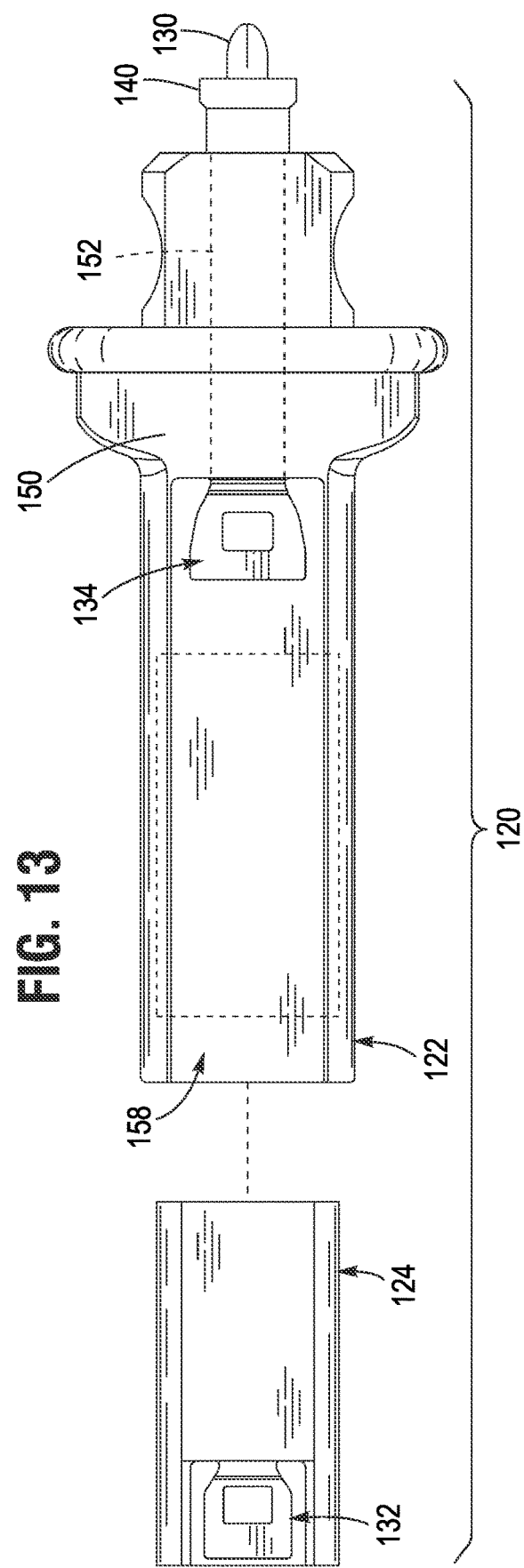
FIG. 13 is an exploded plan view thereof.

The internal housing 144 includes a relatively wide distal end 150 completely surrounding a lumen 152 therethrough, shown in FIG. 13, that also passes through the external handle 142 and distal hub 140 for passage of the catheter 128. On its proximal end, the housing 144 includes an elongated chute that extends into the bag 126. The chute is closed on three sides by a floor 154 and two sidewalls 156 that are slightly concave on their inner faces. The chute defines a longitudinal slightly oval channel 158 therein for reciprocal movement of the movable member 124. The movable member 124 is shown within the channel 158 in FIG. 12 and exploded therefrom in FIG. 14, with an outline thereof in phantom the channel 158.

Figure 15A:
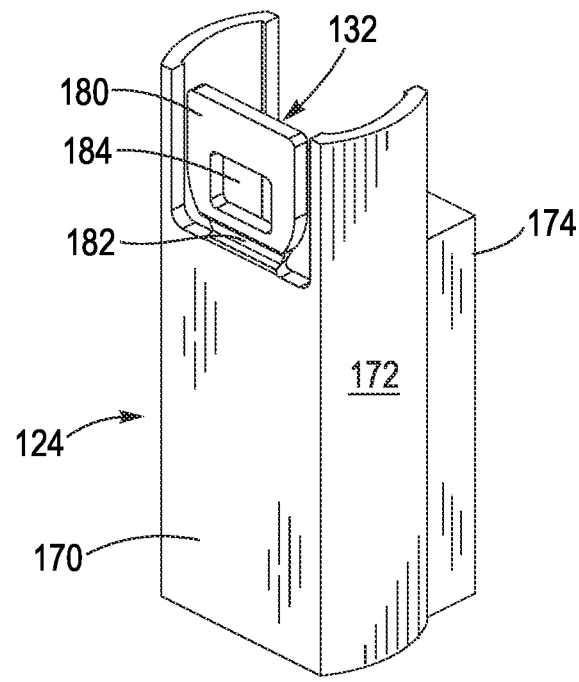
Figure 15B:
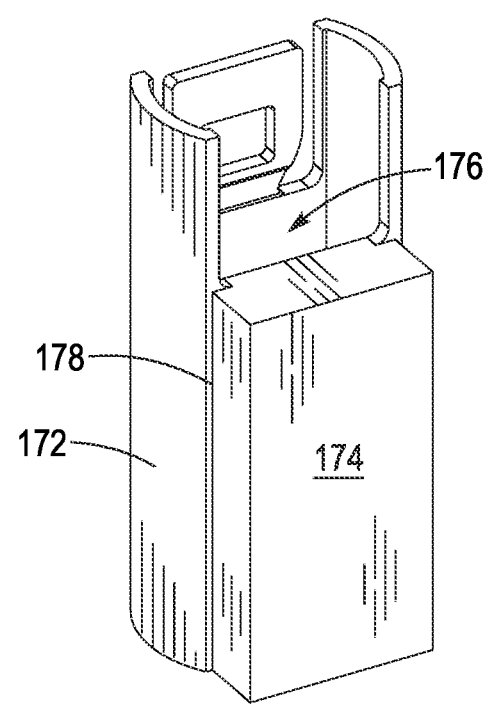
Figure 15C:
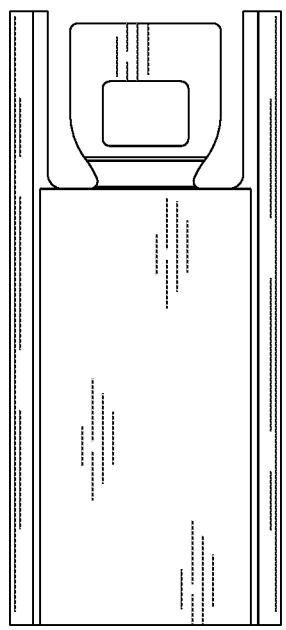
Figure 15D:
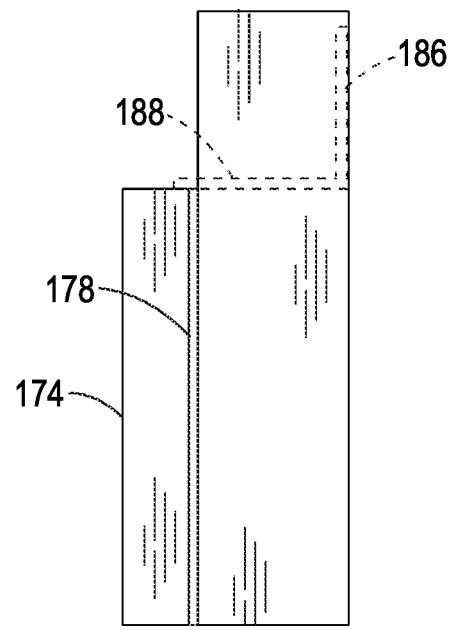

The second or outer movement control device 134 comprises a cantilevered tab 160 connected to one side of the wide distal end 150 at a hinge 162, preferably a living hinge. Instead of a discrete main body, as with the movement control devices described above, the rest of the base member 122 serves as the main body. The tab 160 has an orifice 164 therethrough that serves to alternately slide over or catch on the catheter 128. The tab 160 generally bends from the longitudinally-aligned position 166 as shown in FIGS. 12 and 15D down into the channel 158 into engagement with the catheter 128 and to a misaligned position 168 angled about 90° from longitudinal.

As seen in FIGS. 14A-14D, the movable member 124 has a generally tubular housing formed by a floor 170, two sidewalls 172 and an upper finger pad 174. The two sidewalls 172 are slightly outwardly convex so as to closely fit within the slightly oval channel 158 defined by the chute of the base member 122. The housing defines a longitudinal throughbore 176 for passage of the catheter 128. The upper finger pad 174 is separated from the two sidewalls 172 by a pair of outwardly-directed longitudinal grooves 178 whose purpose will be explained below.

Figure 14A:
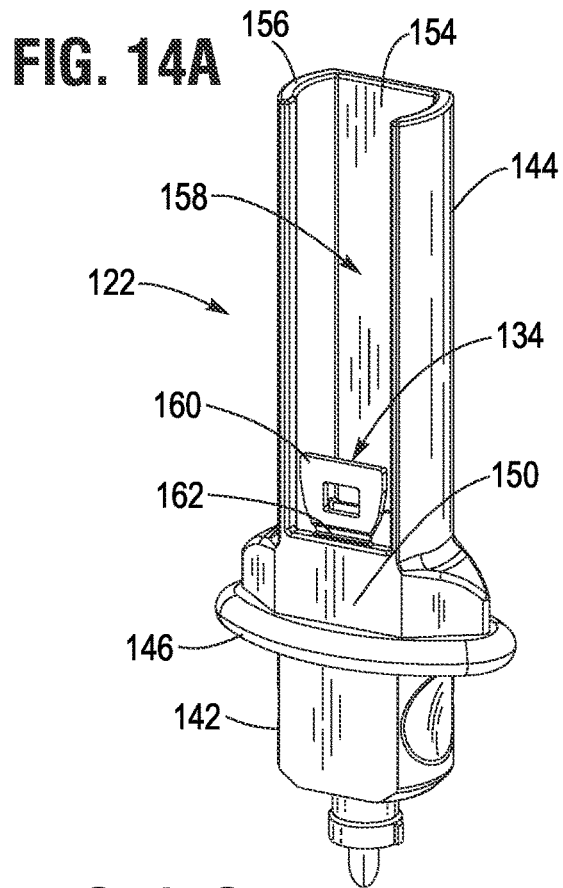
FIGS. 14A-14D are various views of an outer base member that forms a part of the integrated assembly of FIG. 12, and FIGS. 15A-15D are various views of a smaller movable member that slides within the base member.
Figure 14B:
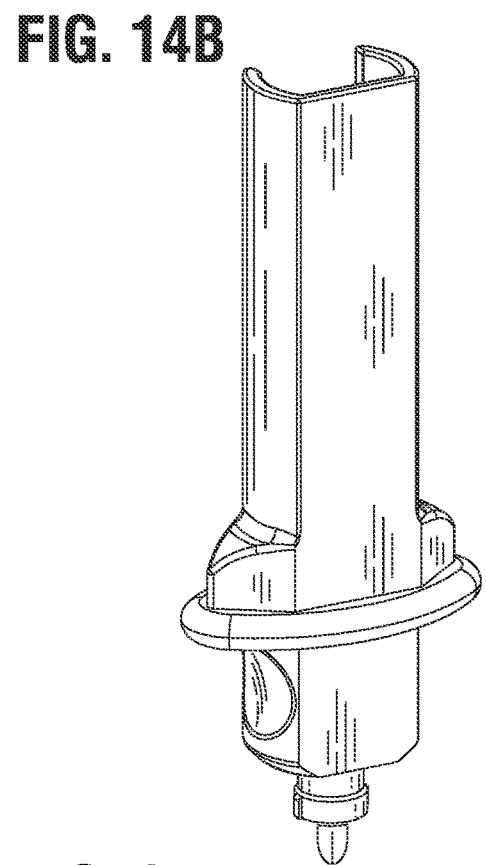
Figure 14C:
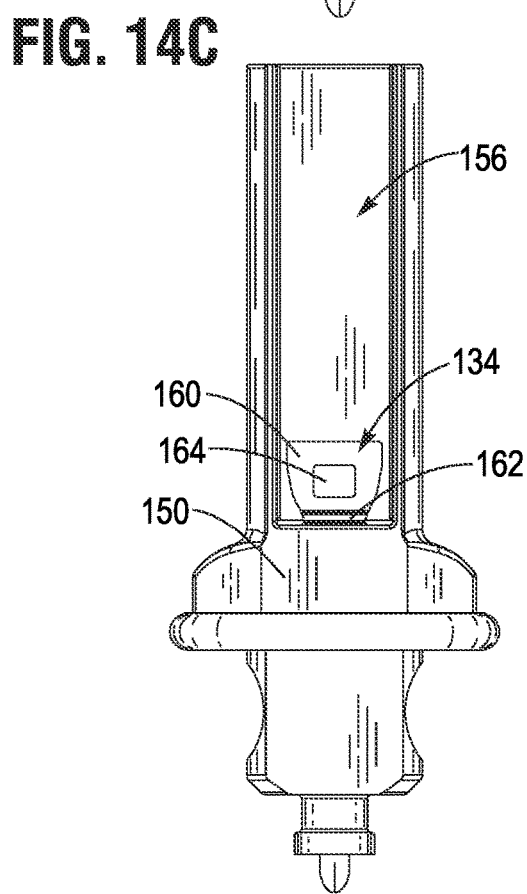
Figure 14D:
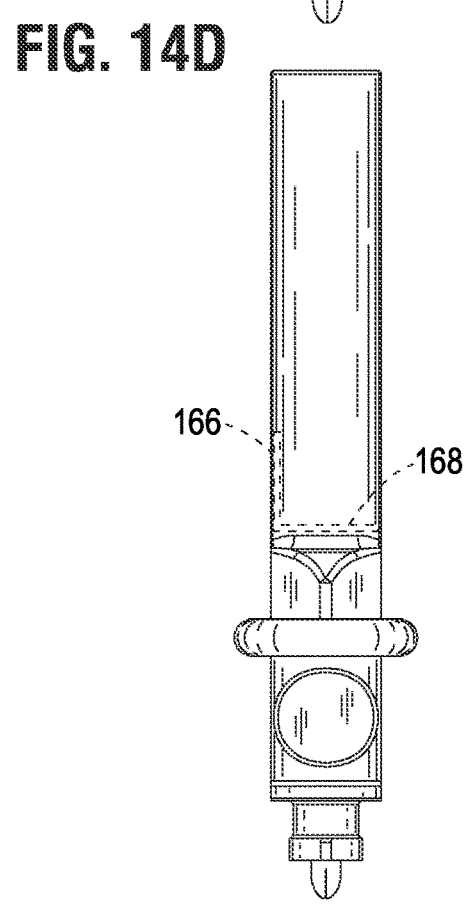

The first or inner movement control device 132 comprises a cantilevered tab 180 connected to the floor 170 at one side of the generally tubular housing with a hinge 182, preferably a living hinge. Instead of a discrete main body, as with the movement control devices described above, the rest of the movable member 124 serves as the main body. The tab 180 has an orifice 184 therethrough that serves to alternately slide over or catch on the catheter 128. The tab 180 generally bends from the longitudinally-aligned position 186 as shown in FIGS. 12 and 14D up into the throughbore 176 into engagement with the catheter 128 and to a misaligned position 188 angled about 90° from longitudinal. As seen best in FIG. 14B, the finger pad 174 terminates short of the two sidewalls 172 so that the tab 180 contacts one end of the finger pad 174 when in the misaligned position 188.

Now with reference back to FIGS. 12 and 13, the movable member 124 fits closely within the slightly oval channel 158 defined by the chute of the base member 122, with the first or inner movement control device 132 on an end opposite the second or outer movement control device 134. The outwardly-directed longitudinal grooves 178 flanking the upper finger pad 174 receive longitudinal edges of the two sidewalls 156 on the chute of the base member 122 so that the movable member 124 is held and guided hereby.

To assemble the sterile closed intermittent urinary catheter system, the movable member 124 is first inserted into the oval channel 158 of the base member 122. Next, the two tabs 160, 180 forming the movement control devices 132, 134 are bent so that they extend across the respective passageways defined by the base member 122 and the movable member 124. Once bent, the catheter 128 may pass through the orifices 164, 184 of the tabs 160, 180 and positioned with its distal tip just inside the introducer tip 130, as seen in FIG. 11. The outer sterile bag 126 may be formed around the assembly 120, preferably after positioning of the catheter 128 therein.

When assembled, the user may easily manipulate the finger pad 174 through the flexible plastic of the bag 126 while simultaneously holding still the base member 122, such as by grasping the ergonomic external handle 142. This operation may even be done with one hand. To help move the finger pad 174, rubber tape or other such friction-inducing material may be added to the exterior of the bag over the pad, and various other solutions are disclosed herein. The generally rectangular lateral cross-section of the integrated assembly 320 aids in these various movements by presenting resistance to rotation about the longitudinal axis and also a flatter profile for the user to compress between his or her hands.

Feed Lock

In addition to facilitating advancement of a catheter from a closed intermittent urinary catheter system, the present application also discloses a safety measure to help prevent premature expulsion of the catheter from the sterile bag. As with most such systems, once an outer packaging is removed, the catheter may be advanced. If the user has not yet positioned and inserted an introducer tip into the urethra, there is the possibility that the catheter may be prematurely advanced and then come into contact with the exterior of the urethra, an area with many germs. If the user inadvertently picks up bacteria from outside the urethra and transfers it into the urethra, an infection may ensue.

FIG. 16 illustrates a system of a sterile catheter package 200 having a flexible bag 202 defining a reservoir therein and containing a catheter 204 and a dispensing system with a first movement control device 206 and a second movement control device 208. The package 200 and first and second movement control devices 206, 208 are as described above, with the latter facilitating advancement of the catheter 204 from within the reservoir and out through an outlet 210 which may include an introducer tip 212.

The system further includes a safety device in the form of a third movement control device 220 mounted over the catheter 204 adjacent its distal tip. Unlike the other two, the orientation of the third movement control device 220 is reversed with a locking tab 222 located on a distal side of a main body 224. The third movement control device 220 is mounted close to the outlet 210 and in particular just inside a collapsible extension 226 of the bag 202. The locking tab 222 has an orifice through which the catheter 204 extends and when the catheter 204 is displaced distally relative to the third movement control device 220 it tends to pivot the locking tab 222 away from the main body 224 such that the orifice becomes misaligned with the catheter axis—the locked position. Thus, in the configuration shown in FIG. 16 the third movement control device 220 prevents distal movement of the catheter 204 and thus prevents the catheter from being dispensed from within the bag 202.

To operate the system, the user first inserts the introducer tip 212 into the urethra and applies pressure by manipulating the bag 202 such as with its handles. This pressure produces a reaction force from the urethra opening, indicated by the force arrows 230 in FIG. 16A, which collapses the extension 226 of the bag 202. Contact of the collapsing extension 226 pivots the locking tab 222 toward or against the main body 224 such that the orifice becomes aligned with the catheter axis—the unlocked position. At this stage, manual coordinated movement of the first and second movement control devices 206, 208 by grasping through the bag 202 advances the catheter 204 from within the bag. Since the catheter 204 emerges directly into the urethra by virtue of the pre-inserted introducer tip 212, no bacteria is carried into the urethra.

FIG. 17A is a front view of another embodiment of a packaged catheter 240 having a catheter 241 housed within a sterile bag with an outlet end 244. As with the sterile catheter package 200, a safety device in the form of a movement control device 242 mounts within the sterile bag close to the outlet 244, and in particular just inside a collapsible extension 246 of the bag. The movement control device 242 works in the same manner as described above. FIG. 17B shows collapse of the extension 246 of the bag from reaction pressure 248 against the urethra such that the movement control device 242 opens or unlocks and the catheter 241 may be advanced. In this embodiment, the outlet 244 features a solid cap member 249 having an inwardly-extending tubular portion that contacts the locking tab of the movement control device 242.

The packaged catheter 240 also has an integrated assembly 250 of a pair of movement control devices 252, 254 mounted therein for advancing a catheter. The integrated assembly 250 may be the same as the integrated assembly 120 described above with respect to FIG. 11, and includes a larger base member 256 and a smaller movable member 258 arranged to slide within the base member. The smaller movable member 258 has a finger pad on its front surface that may be manipulated through the flexible bag, or the finger pad may be adhered to an inner side of the outer wall of the bag. Reciprocal sliding of the movable member 258 within the base member 256 advances the catheter 241 out of the outlet 244 of the sterile bag.

FIG. 18 is a perspective view of an integrated assembly 320 of a pair of movement control devices within relatively sliding housings which is similar to the integrated assembly 120 described above within respect to FIG. 12. The integrated assembly 320 includes a larger base member 322 and a smaller movable member 324 arranged to move within the base member. The base member 322 may be secured to one end of a sterile bag, such as schematically shown at 126 in FIG. 11, and defines an exterior handle grip of the integrated assembly 320. A catheter (not shown) passes longitudinally through the assembly 320 and typically is positioned with its distal tip just inside of an introducer tip 330 in a stored position.

A first or inner movement control device 332 forms a part of the movable member 324 while a second or outer movement control device 334 forms a part of the base member 322. It will be understood that relative displacement of the movement control devices 332, 334 advances the catheter in the "inchworm" manner depicted in FIGS. 10A-10C.

As in the detailed views of the prior embodiment of FIGS. 12-15, the larger base member 322 includes a distal hub 340 from which the introducer tip 330 projects. The hub 340 in turn is preferably molded together with an ergonomic external handle 342 and an internal housing 344 which are separated by a flange 346. When assembled with the sterile bag, the handle 342 is outside while the housing 344 is inside, with the bag preferably adhered or heat sealed to the interior of the flange 346, such as seen in FIG. 11.

The movable member 324 has a generally tubular housing topped by an upper finger pad 350. The upper finger pad 350 has an alternative configuration than flat as shown, with two spaced apart and laterally-extending raised bars 352 on an upper surface. The bars 352 in conjunction with the recessed area therebetween facilitates purchase of a person's finger, thumb, or other portion of the hand or arm when sliding the movable member 124 back-and-forth through the bag. That is, the bars 352 project upward and thus form an easy-to-manipulate finger pad 350. Of course, other such projections upward from a flat finger pad may be used, such as an "X" pattern or the like. The finger pad 350 is manipulated by the user through the flexible bag, and may also be adhered to an inner surface of the bag to avoid slippage therebetween.

FIGS. 19A and 19B are perspective views of the integrated assembly 320 of FIG. 18 mounted to a sterile bag with alternative friction-enhancing pads 360, 370 in operative relationship with the finger pad 350. The friction-enhancing pads 360, 370 are desirably adhered to an outer panel 380 of the bag directly over the finger pad 350. The friction-enhancing pad 360 of FIG. 19A has a six-sided polygonal shape which maximizes surface area over the finger pad 350, while the friction-enhancing pad 370 of FIG. 19B has a double-headed arrow shape to indicate the direction of sliding movement. Alternatively, a double-headed arrow may be printed onto the polygonal friction-enhancing pad 360. The friction-enhancing pads 360, 370 may be made of various compressible materials, such as rubber, closed-cell foam, or the like, or may be formed of a plastic with friction-enhancing features provided on the upper surface, such as bumps, ribs, a gritty layer, or others. Preferably the friction-enhancing pads 360, 370 are flexible to conform to the bag and assist the user in transmitting force to the underlying finger pad 350. As before, the finger pad 350 may be adhered to an inner surface of the bag to avoid slippage therebetween.

FIGS. 19C and 19D are perspective views of the integrated assembly 320 of FIG. 18 mounted to a sterile bag with the alternative friction-enhancing pads 360, 370 supplemented with loops or straps 364, 366. The straps 364, 366 may be used to help a user grasp and linearly reciprocate the finger pad 350.

Figure 20B:
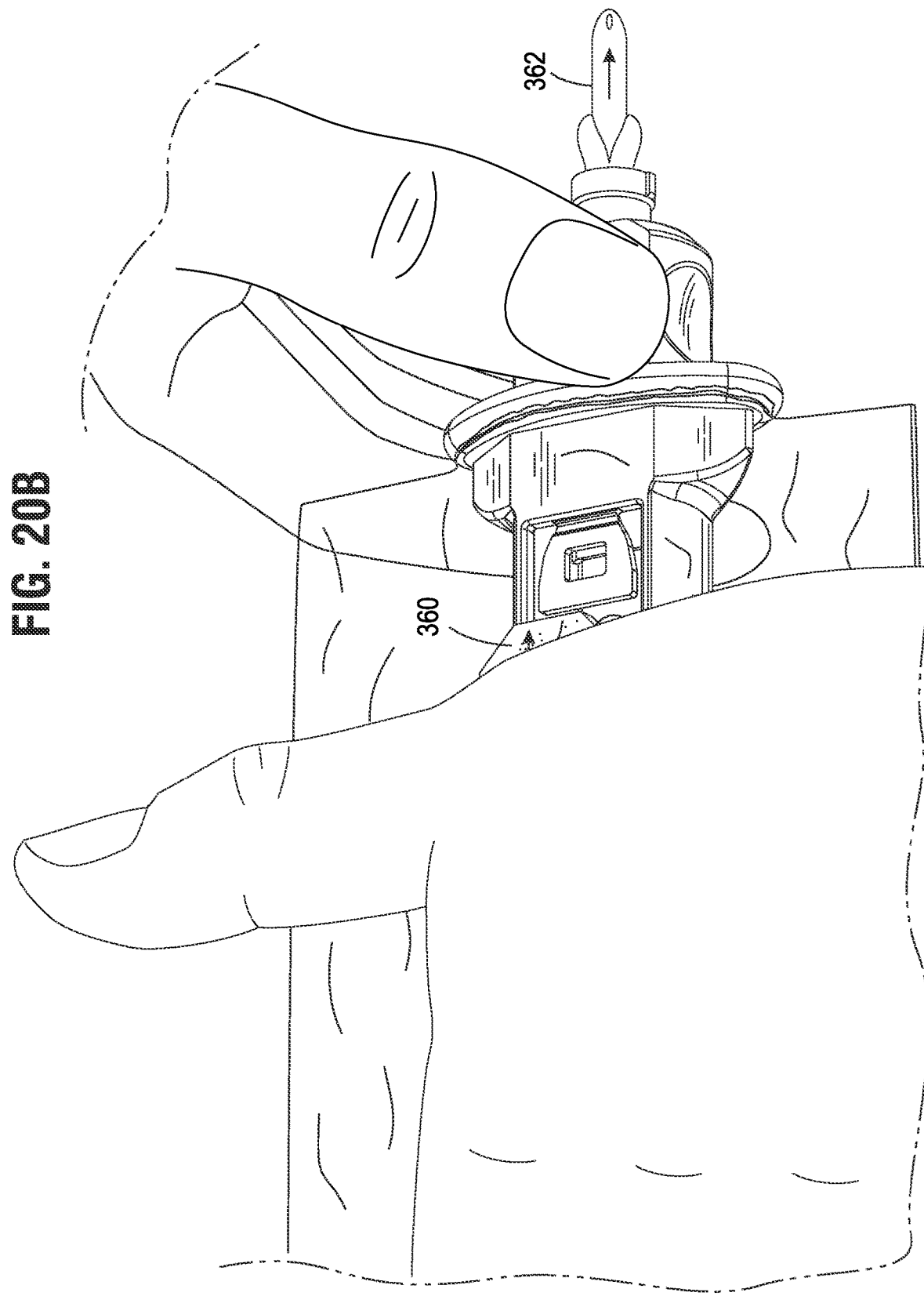

FIGS. 20A-20D are perspective views of the integrated assemblies 320 of FIGS. 19A and 19C mounted to an outer panel of a sterile bag showing a variety of different ways to grasp and reciprocate the finger pad 350 to advance the catheter from within the bag. For instance, FIG. 20A shows a user holding the outlet end of the bag in one hand with the palm and fingers under the integrated assembly 320 and the thumb in contact with the friction-enhancing pad 360. Back-and-forth movement of the thumb on the friction-enhancing pad 360 advances the catheter 362 out of the sterile bag.

FIG. 20B shows a two-handed operation, where the right hand grasps and steadies the integrated assembly 320 while the left hand reciprocates the friction-enhancing pad 360 and underlying finger pad 350. Some users have a difficult time with dexterity, and so the user may contact the wide friction-enhancing pad 360 with the heel of his or her palm.

In FIG. 20C the user merely sandwiches the integrated assembly 320 between his or her two hands, without grasping at all. One or more fingers may be inserted through the strap 364 to gain purchase on the finger pad 350 without the need for grasping. Back-and-forth movement of the hand in contact with the friction-enhancing pad 360 and within the strap 364 advances the catheter 362.

Figure 20D:
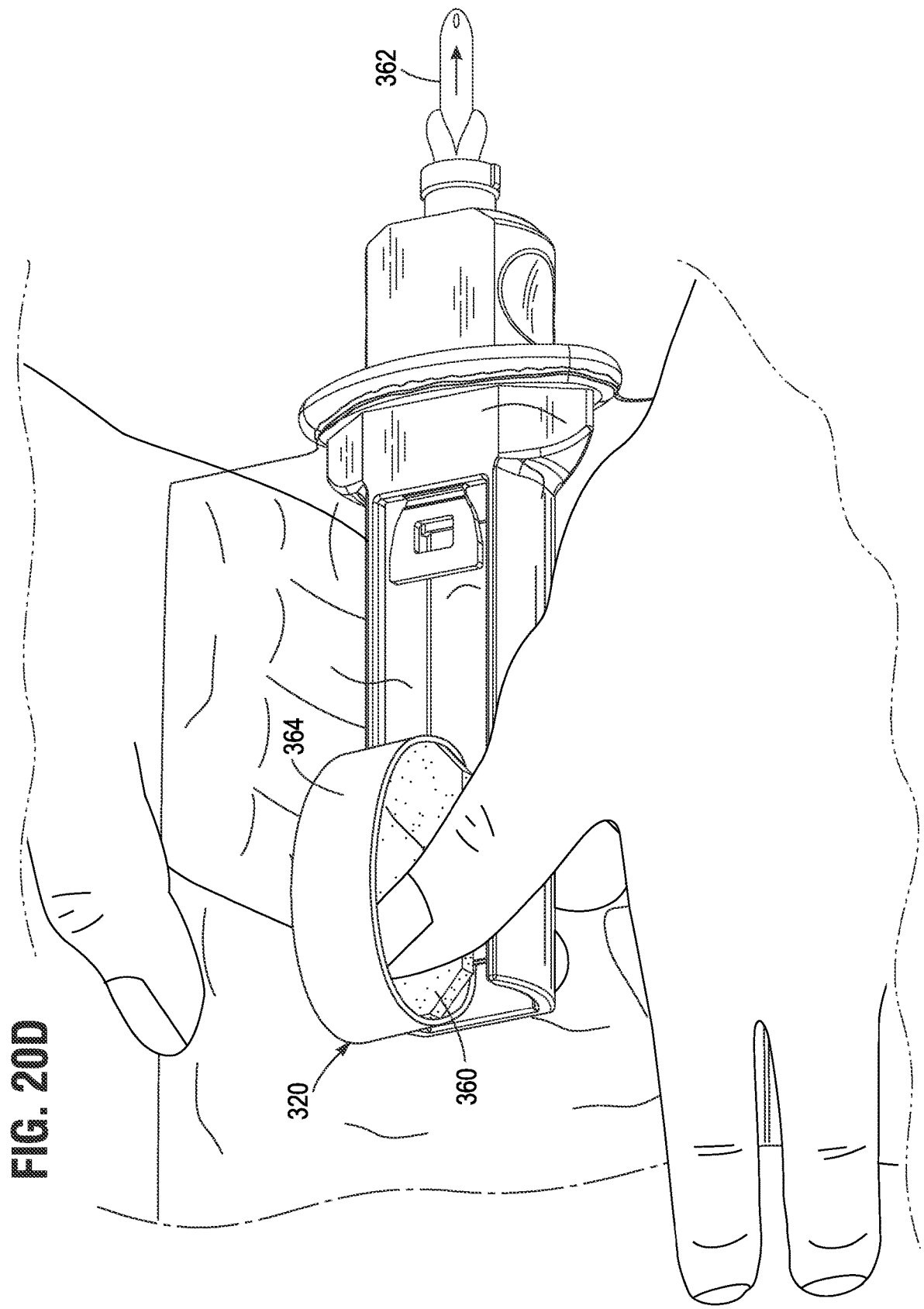

Finally, FIG. 20D illustrates a still further possible configuration where the user stabilizes the integrated assembly 320 from underneath with the right hand while manipulating the friction-enhancing pad 360 with the thumb of the left hand through the strap 364. It should be noted again that the generally rectangular lateral cross-section of the integrated assembly 320 aids in these various movements by presenting resistance to rotation about the longitudinal axis and also a flatter profile for the user to compress between his or her hands.

FIGS. 21A and 21B are front and rear views of a further embodiment of a packaged catheter 400 incorporating an integrated assembly of a pair of movement control members of a dispensing system 402 and a catheter 404 fully retained within the packaging. As described above, the packaging desirably includes a flexible bag 406 having top and bottom sheets which are sealed around their outer edges 408. In the illustrated embodiment, the dispensing system 402 is positioned at one longitudinal end of the elongated rectangular bag 406 (an outlet end) so that the catheter 404 may be extended therefrom. The dispensing system 402 may be constructed as described above, or may include alternative movement conversion structure defined below which enables extension or retraction of the catheter 404. A sterile cap 410 having a pull ring thereon is typically coupled to the exposed end of the dispensing system 402 to maintain sterility of the catheter therein.

FIG. 22 is an exploded assembly view of the packaged catheter 400 of FIG. 21A, and illustrates the various components. Specifically, the dispensing system 402 includes an elongated base member 412 having a first movement control device 414a, and a smaller movable member or slider 416 having a second movement control device 414b. The base member 412 and the slider 416 may be constructed as described above with respect to FIGS. 11-15, and reference may be had to that earlier description for details. As mentioned, the base member 412 is secured at one longitudinal end of the bag 406, and in particular has a hub 418 projecting out from the bag. An introducer 420 attaches to a nipple 422 of the hub 418, over all of which the sterile cap 410 is secured.

The packaged catheter 400 includes a number of ergonomic features which facilitate deployment and usage of the catheter 404, especially by those with limited dexterity. First of all, the base member 412 and the slider 416 are adhered to the interior surfaces of the rear and front sheets of the bag 406, respectively. A slider direction indicator 424 shown in FIG. 21A and exploded in FIG. 22 is adhered to the exterior surface of the front sheet of the bag 406. Likewise, a holding strap 426 shown in FIG. 21A and exploded in FIG. 22 is adhered to the exterior surface of the rear sheet of the bag 406. The holding strap 426 may be constructed in shape like the holding straps 364, 366 described above with respect to FIGS. 19C-19D. The indicator 424 may be formed in a variety of ways, such as described above with respect to FIGS. 19A-19D and 20A-20D. However, a particularly useful variant is to form the indicator 424 out of a compressible and/or frictional material such as foam having a symbolic movement shape such as the double arrow shown. It should be mentioned here that providing a movement control member which moves relative to a stationary control member need not be a linear slider as illustrated, and could be formed in a variety of ways such as described below with respect to FIGS. 30-34.

In any event, the direction indicator 424 is adhered directly over the slider 416, which in turn is adhered to the interior of the bag 406, and thus moving the direction indicator moves the slider. At the same time, the user can grasp the relatively narrow bag 406 with one hand and his or her fingers passed through the holding strap 426 on the rear of the bag 406, which is secured to the base member 412. The thumb or a second hand may be used to manipulate the slider 416 and movable control member 414b. As explained above, back and forth movement of the slider 416 incrementally advances the catheter 404 out of the bag 406. Namely, both the movement control members 414a, 414b facilitate one way movement of the catheter 404. The provision of the direction indicator 424 and holding strap 426 on opposite sides of the bag 406 greatly enhances the control ability of the user in advancing the catheter 404.

With reference again to FIGS. 21A and 21B, the bag 406 has a number of finger holes which also help with handling and usage. A first finger hole 428a is provided at an end of the bag 406 opposite the outlet end, preferably inset at one corner thereof. A pair of second finger holes 428b, 428c are formed at opposite corners of the outlet end of the bag 406. The finger holes 428 are sized to receive at least one and preferably two fingers of an average user, and are cut from within regions 408 of the two sheets of the bag that are sealed together. Additionally, a line of perforation 430 extends longitudinally from the outlet end of the bag 406 along the sealed region adjacent one of the second finger holes 428b, and then angles toward a lateral side edge.

FIG. 23 is an image of one corner 432 of the bag 406 being torn away at the line of perforation 430 to form a drain. The user may grasp both of the second finger holes 428b, 428c to easily tear away the corner of the bag 406 past the sealed regions 408 until an opening or drain is formed. Urine within the bag 406 can then be drained into a waste receptacle such as a toilet. The first finger hole 428a may be used to suspend the bag 406 over the toilet, either manually or by hanging the bag on a convenient hook which may be handy.

FIG. 24 is an exploded perspective view and FIGS. 25A/25B and 26A/26B are plan and sectional views of an integrated assembly of a pair of movement control devices within relatively sliding housings, including structure enabling conversion of the movement control devices for reverse movement of a catheter. The integrated assembly includes a stationary base member 440 and a movable member or slider 442. The base member 440 has an outlet hub 444 with an elongated channel 446 extending rearwardly therefrom. The movable slider 442 has a body 448 which is sized to closely fit and slide longitudinally within the channel 446, as described above. The slider 442 has a hollow through bore, as does the outlet hub 444, such that a catheter 450 shown in FIGS. 27A-27C may be passed longitudinally through the integrated assembly.

Each of the base member 440 and slider 442 has a movement control device incorporated therein which enables advancement of the catheter 450. Namely, a first movement control device 452a is provided on the base member 440, and a second movement control device 452b is on the slider 442. As explained above, one preferred movement control device is a small tab or flap which is pivotally connected to the respective host body having an opening 454 therethrough for the catheter 450. The one-way movement control of the flaps was described above with respect to FIGS. 10A-10C, and is thus not repeated here. The first and second movement control devices 452a, 452b are initially arranged to cause advancement of the catheter 450 from the outlet end of the assembly, and thus the sterile package.

In some cases, the user may wish to withdraw the catheter 450 back into the sterile package. Accordingly, the integrated assembly incorporates structure which permits the direction of each of the movement control devices 452a, 452b to be reversed. In particular, each of the base member 440 and slider 442 has structure which enables the flap-like movement control devices 452a, 452b to pivot in an opposite direction. Both of the flaps 452a, 452b are shown in FIGS. 24-25 lying flat and extended to the left. By angling the flaps 452a, 452b upward the catheter 450 may be passed through each of the openings 454, as seen in FIG. 27A. As long as the flaps 452a, 452b are not pivoted more than 90°, they will function to advance the catheter out of the sterile package.

FIG. 26A includes an enlargement in which one of a pair of flexible tabs 456 may be seen extending inward into the channel 446. The flexible tabs 456 are provided on opposite sides of the channel 446, and extend inward far enough to interfere with pivoting movement of the first flap 452a. Preferably, the tabs 456 are wedge-shaped to facilitate passage of the flap 452a in one direction, but inhibit the reverse pivoting movement. In a similar manner, the slider 442 features a pair of flexible tabs 458 which extend inward on opposite lateral sides of the body 448. Again, the flexible tabs 458 project far enough to interfere with pivoting movement of the second flap 452b, and are again preferably wedge-shaped. As will be explained below, manual manipulation of the integrated assembly converts the flaps 452a, 452b from their catheter-forward movement orientation, to a catheter-rearward movement orientation.

FIGS. 27A-27C are several steps showing conversion of the integrated assembly of FIG. 24 from forward to reverse movement of the catheter 450. Prior to a discussion of this conversion, it will be noted that the slider 442 has a forward nose 460 on an end that faces into the channel 446 of the base member 440. The nose 460 is adapted to contact and pivot the first flap 452a.

FIG. 27A shows the integrated assembly in its conventional catheter-forward orientation, with the first flap 452a proximally oriented at an angle of roughly 45° CCW, and the second flap 452b proximally oriented at an angle of roughly 45° CW. These angular orientations are as seen from looking at the side of the integrated assembly with the slider 442 on top and the outlet end to the right. The slider 442 is shown moving to the right, which "pulls" the second flap 452b into its angled orientation such that the opening 454 therein catches on the catheter 450 and moves it to the right, as indicated. At the same time, movement of the catheter through friction with the opening of the first flap 452a pivots the flap CCW to a more vertical orientation, which permits passage of the catheter.

After full advancement of the catheter 450, the user may wish to withdraw the catheter from within the urethra and discard the package. However, it is often difficult for a user, especially one with limited dexterity, to handle the now lubricated length of catheter along with the full bag 406. Consequently, reversing movement of the catheter 450 through the integrated assembly so as to retract it into the bag 406 is desirable.

To reverse movement of the catheter 450, the user pushes on the second flap 452b, as indicated in FIG. 27B. This pivots the second flap 452b in a CW direction past the opposed flexible tabs 458, which are preferably located at about the point that the second flap reaches 90°, to a distal orientation. In the process, pushing on the second flap 452b pushes the slider 442 to the right until the forward nose 460 (see FIG. 25A) contacts and pivots the first flap 452a CCW. Eventually, the first flap 452a pivots past the opposed flexible tabs 458 within the channel 446, to a distal orientation, again which is preferably about a 90° orientation of the first flap. Now the flaps 452a, 452b are distally orientated and prevented from pivoting back to their original orientations, and function in the opposite direction to cause proximal retraction of the catheter.

FIG. 27C shows leftward movement of the slider 442 which causes retraction of the catheter 450. In particular, the leftward movement of the slider 442 causes the second flap 452b to pull the catheter 450 to the left, and then the slider can be moved to the right without pushing the catheter back out again. This ability to reverse movement of the catheter in conjunction with the ergonomic movement pads and indicators described above greatly increases control of the urinary catheter package.

Figure 28:
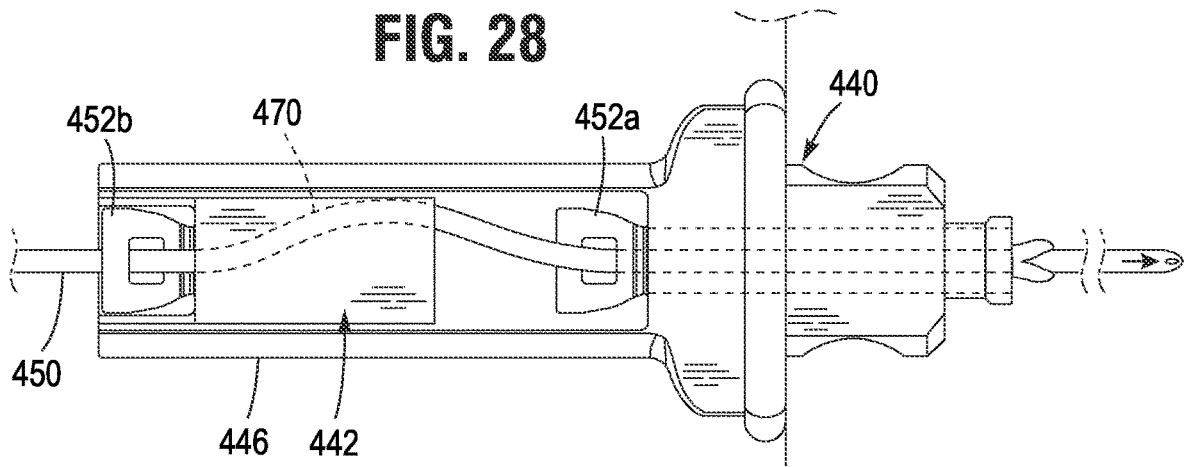
FIG. 28 is a plan view of the integrated assembly of FIG. 24 showing potential buckling of smaller catheters therein.

FIG. 28 is a plan view of the integrated assembly of FIG. 24 showing potential buckling of smaller catheters therein. That is, as the slider 442 moves to the right, which moves the catheter 450 to the right through the urethra, resistance may cause a region of buckling 470 where the catheter is unsupported in the hollow slider and channel 446. Urinary catheters have different tube sizes for different patients, typically between 8-18 French (3 Fr=1 mm OD, so 8 Fr=2.7 mm).

Figure 29A:
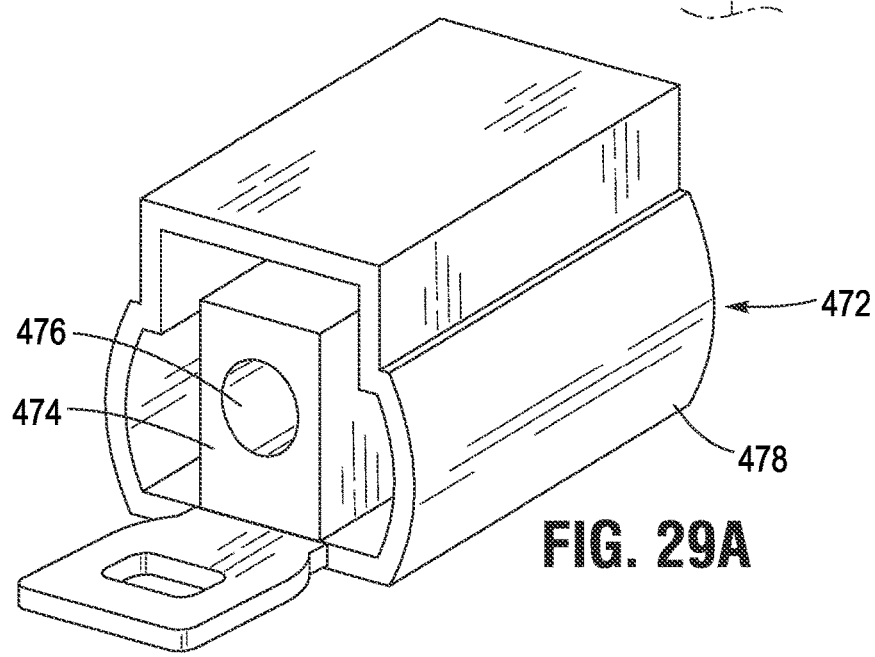
FIGS. 29A and 29B are perspective and elevational views, respectively, of an alternative slider with catheter reinforcing structure.
Figure 29B:
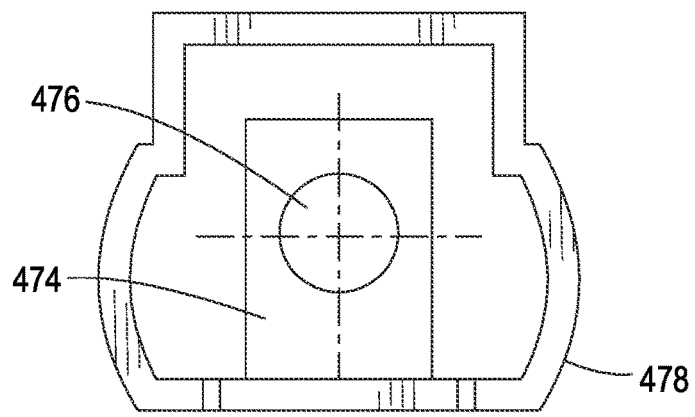

To provide greater support for smaller catheters, reinforcement structure within the slider 442 is desirable. FIGS. 29A and 29B are perspective and elevational views, respectively, of an alternative slider 472 with such catheter reinforcing structure. Namely, a block 474 of material having a tunnel 476 may be incorporated within the otherwise hollow slider body 448. Illustrated embodiment, the block 474 is somewhat thick, but it may be formed with thin walls like the outside of the slider body 478 for the purpose of manufacturing. The block 474 and tunnel 476 thus provide a closely-fitting guide for the smaller catheters which prevents them from buckling within the slider 442, and thus more effectively aligns and pushes the catheter through the assembly and into the urethra. In one embodiment, the reinforcing structure may provide a tunnel 476 having a diameter of 10 French, so as to accommodate smaller 8 and 10 French catheters, with larger sizes being sufficiently robust to obviate the need for reinforcement.

Figure 30A:
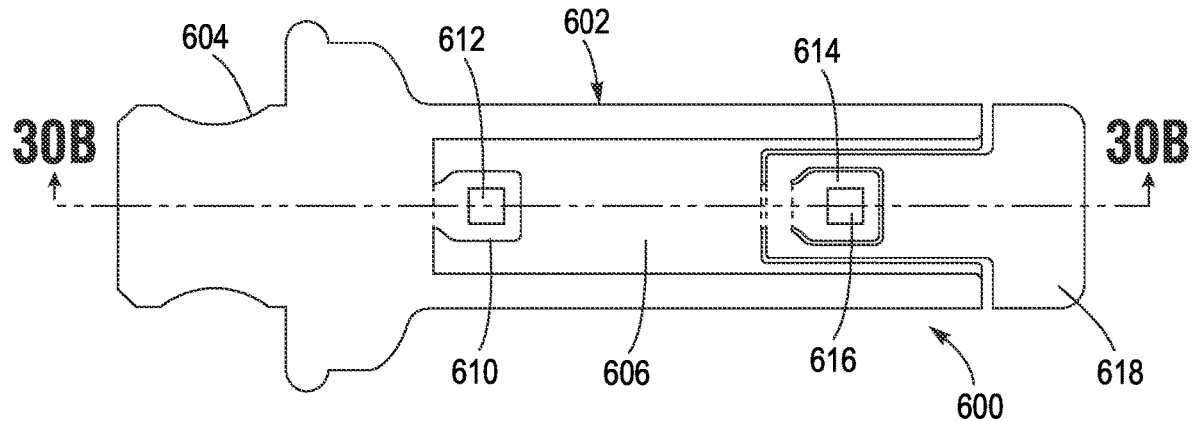
FIGS. 30A-30C are plan and sectional views of an alternative integrated assembly of a pair of movement control devices mounted within a handle grip component for facilitating single-handed dispensing of the catheter.
Figure 30B:
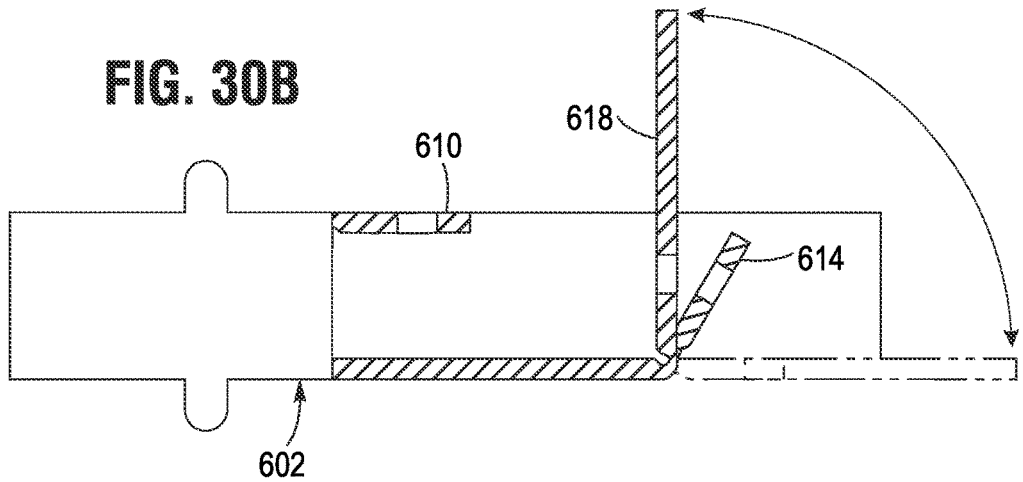
Figure 30C:
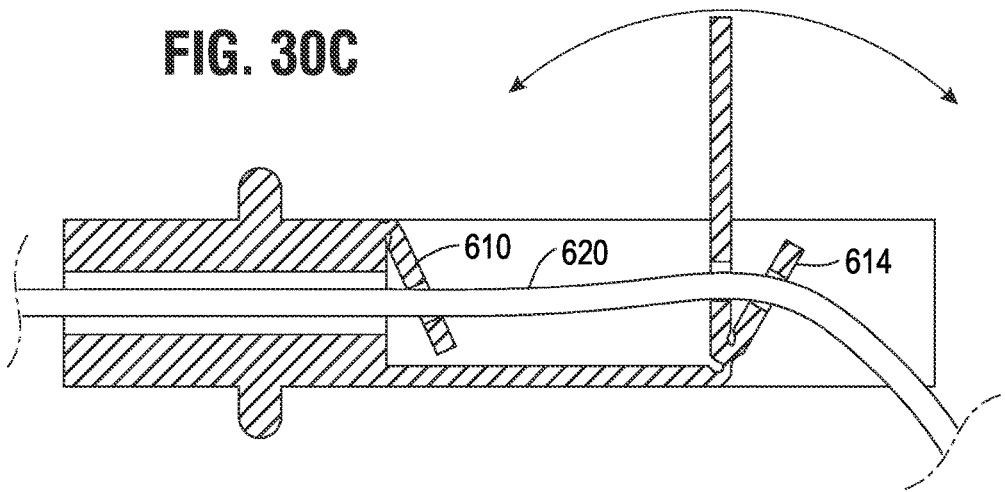

FIGS. 30A-30C are plan and sectional views of an alternative integrated assembly 600 having a pair of movement control devices mounted within a handle grip 602 for facilitating single-handed dispensing of the catheter. The assembly 600 is similar to the integrated assembly 120 shown in FIG. 11, albeit molded as a single piece. The handle grip unit 602 defines an outlet fitting or housing 604 on one end and an elongated channel 606 on the other end between two side walls (not numbered). The assembly 600 may be positioned within an interior cavity of the urine collection bag (not shown), and the outlet housing 604 preferably extends out of the bag.

A first movement control device in the form of a flap 610 and aperture 612 is connected via a living hinge to the housing 604, opposite a floor of the channel 606. A second movement control device in the form of a flap 614 and aperture 616 mounts via a living hinge to a larger tab 618. The tab 618 is a rectilinear piece connected via a living hinge to the floor of the channel 606. The tab 618 can pivot up out of the channel 606 and the flap 614 can pivot with respect to the tab 618.

In use, a catheter 620 is fed longitudinally through the assembly 600 through a bore in the housing 604 and along the channel 606. The catheter 620 passes through both apertures 612, 616 (which are desirably square or rectangular). As explained above, when the flaps 610, 614 pivot to be perpendicular to the catheter 620, they permit sliding movement therebetween, but when either flap 610, 614 is angled with respect to the catheter 620, sliding movement is impeded.

Reciprocal movement of the second movement control device as indicated by the double-arrow in FIG. 30C acts to advance the catheter 620 incrementally. That is, as the tab 618 is rotated upward (CCW), the flap 614 pivots from friction with the catheter 620 to an angled orientation, thus grabbing on the catheter and moving it to the left. The flap 610 pivots to a perpendicular orientation permitting the catheter 620 to slide therethrough. Conversely, when the tab 618 is rotated downward (CW), the flap 614 pivots into alignment with the tab, and to a perpendicular orientation with respect to the catheter 620, allowing sliding movement therebetween. At the same time, the first flap 610 catches on the catheter so that it does not retract. The second movement control device (tab 618/flap 614) is thus reset for a subsequent incremental movement of the catheter. A user may manipulate the tab 618 through the flexible urine collection bag, which may be shaped to facilitate such manipulation.

FIG. 31A is an assembled view of a squeezable one-piece molded catheter feeder 650 incorporated into a urine collection bag 652. The collection bag 652 has a generally rectangular configuration and an outlet fitting 654 is secured through one lateral edge 656 adjacent an end edge 658. Typically, the collection bag 652 is formed by adhering or welding two sheets of flexible plastic together, and the outlet fitting 654 may be adhered or welded therebetween along the lateral edge 656. An elongated aperture 660 is formed in the collection bag 652 parallel to the lateral edge 656. The catheter feeder 650 resides in the interior of the urine collection 652 between the lateral edge 656 and aperture 660.

The catheter feeder 650 has a pair of finger-like squeezable members 662, 664 resiliently connected together at a living hinge 666. One of the squeezable members 662 attaches to the outlet fitting 654, while the other squeezable number 664 remains free to move within the interior of the collection bag 652. A user may squeeze the members 662, 664 toward each other by passing his or her fingers through the aperture 660 and applying compression to the catheter feeder 650 via his or her thumb on the lateral edge 656, or vice versa.

The catheter feeder 650 incorporates a pair of movement control devices 670, 672, as seen in FIGS. 31B-31F. More particularly, the movement control devices 670, 672 integrate into terminal ends of the squeezable members 662, 664, which are aligned to receive a catheter 674 therethrough. Prior to use, the catheter 674 is retained in a sterile manner within the collection bag 652. As explained above, a forward end of the catheter 674 is initially located within the outlet fitting 654. By squeezing the members 662, 664, the catheter 674 may be expelled out of an outlet port of the fitting 654. Releasing compression on the catheter feeder 650 permits the living hinge 666 to expand the members 662, 664 apart. Repeated compression and release of the catheter feeder 650 incrementally advances the catheter 674. In this regard, the squeezable members 662, 664 and resilient living hinge 666 form a spring-biased coupling member between the movement control devices 670, 672.

The catheter feeder 650 is desirably molded in one piece of a suitable polymer, such as polyethylene or polypropylene. As seen best in FIG. 31C, each squeezable member 662, 664 includes a thin base strip 680 contiguous with and oriented in the same "plane" as the living hinge 666. To provide rigidity, a pair of sidewalls 682 extend alongside each of the base strips 680 except in a region adjacent the living hinge 666. Each of the movement control devices 670, 672 is formed by a small flap 684 contiguous with and in the same "plane" as the base strips 680. Each of the flaps 684 has an aperture 686 extending therethrough, preferably square or rectangular in shape. The flaps 684 may pivot with respect to the base strips 680 so as to alternately permit and impede passage of catheter 674 passing through the apertures 686, as was described previously. It should be noted here that elements that are in the same "plane" refers to their initial as-molded relationship, prior to bending into the functional positions as shown. Elements that are in the same "plane" bend about axes that are parallel.

With reference to FIG. 31D, it should be noted that the terminal end of the first squeezable member 662 features a pair of laterally extending flanges 688 which may assist in coupling the catheter feeder 650 to the outlet port 654. FIGS. 31E and 31F illustrate two different positions A and B of the flap 684 when converting between an as-molded shaped to the position in which the flap 684 functions to regulate passage of the catheter 674.

FIGS. 32A and 32B are plan views of an alternative one-piece molded catheter feeder 690 having a pair of movement control devices 692, 694, and FIG. 32C is a side elevation thereof. The catheter feeder 690 comprises a coupling member 696 in the form of a looped strip which preferably has a relaxed configuration of the elongated oval seen in FIG. 32A, with the movement control devices 692, 694 spaced a first distance part. By pulling lateral sides of the coupling strip 696 apart, as seen in FIG. 32B, the elongated oval shape may be transformed into a more squat oval, thus pulling the movement control devices 692, 694 together to a second distance apart shorter than the first distance. To assist in this transition, a pair of finger rings 698 are desirably molded into each lateral side of the coupling strip 696. The lateral sides of the coupling strip 696 act as springs which tend to return the catheter feeder 690 back to the relaxed elongated oval shape of FIG. 32A. Alternatively, the coupling strip 696 may be molded so as to have a relaxed squat oval shape as seen in FIG. 32B, such that displacing the movement control devices toward and away from another is accomplished by squeezing the lateral sides of the strip together into the elongated oval shape of FIG. 32A, and then releasing them to permit the strip to revert to its relaxed shape again.

As described above, the movement control devices 692, 694 desirably comprise molded flaps 700 having square or rectangular apertures 702 therein. After passing a catheter 704 through the apertures 702, reciprocal movement of the control devices 692, 694 toward and away from one another may advance the catheter in one direction. By placing the catheter feeder 690 within a urine collection bag (not shown), a catheter may be advanced incrementally out of the bag. In this regard, a first one of the movement control devices 692 may be attached to or molded with an outlet fitting 706 which is secured to one edge of the collection bag.

FIGS. 33A and 33B illustrate a further alternative one-piece molded catheter feeder 710 having a coupling member member 712 in the form of a strip of flexible material formed in a loop and a pair of movement control devices 714, 716 secured on opposite sides of the loop. Once again, the catheter feeder 710 may be positioned within an interior cavity of the urine collection bag (not shown), and a first movement control device 714 may be attached to a rigid outlet fitting 718 which extends out of the bag. A catheter 720 may be incrementally advanced from within the collection bag by reciprocal displacement of the movement control devices 714, 716 toward and away from one another. This embodiment functions in a similar manner as the catheter feeder 690 described above, though to advance the catheter 720 the user displaces the second movement control device 716 toward the first movement control device 714 as seen in FIG. 33B. The coupling member strip 712 has a relaxed configuration as in FIG. 33A, such that when the second movement control device 716 is released from its position in FIG. 33B, the strip acts as a spring to convert its shape back to the elongated oval of FIG. 33A.

FIGS. 34A and 34B show a spring-loaded catheter feeder 730 having a pair of separate movement control devices 732, 734 inserted therein. In this configuration, the catheter feeder 730 comprises a compressible coupling member 736 in the form of a tubular body as seen in cross-section in FIG. 34C, preferably made of a flexible polymeric material, such as polyurethane. Flanges 738 formed in the opposite ends of the tubular coupling member 736 define internal slot-like cavities 740 that receive disk-shaped movement control devices 732, 734. Each of the devices 732, 734 has a flap 742 with a square aperture 744 therein that is cantilevered from one side thereof so that the flap may pivot out of the plane of the disk, as seen in FIG. 34B.

A coil spring 746 positioned around the exterior of the tubular coupling member 736 between the flanges 738 biases the body into the elongated shape of FIG. 34A. Squeezing the flanges 738 together brings the movement control devices 732, 734 closer together and advances a catheter 748 that passes through the tubular coupling member 736 in one direction. The catheter feeder 730 is shown in expanded and compressed configurations in FIGS. 34A and 34B. Repeated transitions between the elongated and compressed configurations advance the catheter 748 through the tubular coupling member 736. As before, the catheter feeder 730 may be placed within a urine collection bag (not shown), preferably adjacent an outlet opening, and manipulated between the configurations of FIGS. 34A and 34B to advance the catheter 746 out of the bag.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A closed intermittent urinary catheter system equipped with a catheter dispensing device, comprising:
    a sterile flexible plastic bag having front and rear sides and defining a closed reservoir with an outlet opening;
    a catheter defining a longitudinal axis retained within the reservoir and having a distal insertion tip positioned adjacent to and aimed toward the outlet opening;
    a movable member within the reservoir mounted over the catheter and having a portion adhered to an interior surface on the front side of the bag, the movable member having a movable catheter control device therein that engages the catheter and automatically permits distal movement of the catheter relative to the movable member and automatically resists proximal movement of the catheter relative to the movable member; and
    a base member within the reservoir and configured to receive the movable member for reciprocal movement therein in a distal-proximal direction, the base member being mounted over the catheter distal insertion tip and being fixed to the bag at the outlet opening, the base member having a stationary catheter control device therein that automatically permits distal movement of the catheter relative to the base member and automatically resists proximal movement of the catheter relative to the base member, wherein
    reciprocal movement of the movable member relative to the base member causes the catheter to be advanced distally from the bag through the outlet opening, and the movable member may be displaced relative to the base member by manipulating the movable member through the front side of the bag while holding the base member stationary.

2. The system of claim 1, wherein a first portion of the base member is disposed inside the bag and a second portion of the base member is disposed outside the bag, whereby a passageway through the second portion of the base member defines the outlet opening.

3. The system of claim 1, wherein the movable member includes a flat surface facing toward the bag that is adhered to the interior surface on the front side of the bag.

4. The system of claim 3, further including a friction-enhancing pad adhered to an exterior surface on the front side of the bag directly opposite the finger pad.

5. The system of claim 4, wherein the friction-enhancing pad is a compressible material.

6. The system of claim 4, wherein the friction-enhancing pad has a double-headed arrow indicator thereon to indicate a distal-proximal reciprocal movement direction of the movable member.

7. The system of claim 4, further including a strap sized to receive one or more fingers of a user and attached outside the bag either a) directly over of the friction-enhancing pad or b) outside of the base member on a rear side of the bag with the base member being adhered to an interior surface on the rear side of the bag.

8. The system of claim 1, wherein the movable member is slidably disposed for reciprocal movement in a distal-proximal direction within a channel in the base member.

9. The system of claim 8, wherein the movable member and the base member each have structure that converts the respective catheter control devices therein to cause proximal retraction of the catheter into the bag from reciprocal movement of the movable member relative to the base member.

10. The system of claim 9, wherein each of the catheter control devices includes a pivoting flap having an opening for passage of the catheter and initially having a proximal orientation, and the structure that converts the respective catheter control device to cause proximal retraction of the catheter includes inwardly-projecting tabs that hold the flaps in a distal orientation.

11. A closed intermittent urinary catheter system equipped with a catheter dispensing device, comprising:
   a sterile flexible plastic bag having front and rear sides and defining a closed reservoir with an outlet opening;
   a catheter defining a longitudinal axis retained within the reservoir and having a distal insertion tip positioned adjacent to and aimed toward the outlet opening;
   a movable member within the reservoir mounted over the catheter and having a portion adhered to an interior surface on the front side of the bag, the movable member having a movable catheter control device therein that engages the catheter and automatically permits distal movement of the catheter relative to the movable member and automatically resists proximal movement of the catheter relative to the movable member;
   a friction-enhancing pad adhered to an exterior surface on the front side of the bag directly opposite the movable member; and
   a base member within the reservoir and configured to receive the movable member for reciprocal movement therein in a distal-proximal direction, the base member being mounted over the catheter distal insertion tip and defining a through passage for the catheter, the base member having a stationary catheter control device therein that automatically permits distal movement of the catheter relative to the base member and automatically resists proximal movement of the catheter relative to the base member, wherein
   reciprocal movement of the movable member relative to the base member causes the catheter to be advanced distally from the bag through the outlet opening, and the movable member may be displaced relative to the base member by manipulating the friction-enhancing pad.

12. The system of claim 11, wherein a first portion of the base member is disposed inside the bag and a second portion of the base member is disposed outside the bag, whereby a passageway through the second portion of the base member defines the outlet opening.

13. The system of claim 11, wherein the movable member includes a flat surface facing toward the bag that is adhered to the interior surface on the front side of the bag, and the friction-enhancing pad is flat as well.

14. The system of claim 11, wherein the friction-enhancing pad is a compressible material.

15. The system of claim 11, wherein the friction-enhancing pad has an arrow indicator thereon to indicate a reciprocal movement direction of the movable member.

16. The system of claim 11, wherein the friction-enhancing pad has a double-headed arrow indicator thereon to indicate a distal-proximal reciprocal movement direction of the movable member.

17. The system of claim 11, further including a strap sized to receive one or more fingers of a user and attached outside the bag either a) directly over of the friction-enhancing pad or b) outside of the base member on a rear side of the bag with the base member being adhered to an interior surface on the rear side of the bag.

18. The system of claim 11, wherein the movable member and the base member each have structure that permits the respective catheter control devices therein to cause proximal retraction of the catheter into the bag from reciprocal movement of the movable member relative to the base member.

19. The system of claim 18, wherein each of the catheter control devices includes a pivoting flap having an opening for passage of the catheter and initially having a proximal orientation, and the structure that converts the respective catheter control device to cause proximal retraction of the catheter includes inwardly-projecting tabs that hold the flaps in a distal orientation.

20. The system of claim 11, wherein the bag has a plurality of finger holes around a periphery thereof, including on two corners on one longitudinal end, and the bag includes a perforated line permitting tearing of the bag to open a drain line at one of the corners.

* * * * *